(12) United States Patent
Shah

(10) Patent No.: US 10,963,585 B2
(45) Date of Patent: Mar. 30, 2021

(54) SELF-CONTROLLED DIGITAL AUTHORIZATION OVER COMMUNICATION NETWORKS

(71) Applicant: Netspective Communications LLC, Silver Spring, MD (US)

(72) Inventor: Shahid N. Shah, Silver Spring, MD (US)

(73) Assignee: Netspective Communications LLC, Silver Spring, MD (US)

( * ) Notice: Subject to any disclaimer, the term of this patent is extended or adjusted under 35 U.S.C. 154(b) by 890 days.

(21) Appl. No.: 15/434,942

(22) Filed: Feb. 16, 2017

(65) Prior Publication Data

US 2017/0161517 A1 Jun. 8, 2017

Related U.S. Application Data

(63) Continuation-in-part of application No. 13/607,997, filed on Sep. 10, 2012, now abandoned.

(51) Int. Cl.
*G06F 21/62* (2013.01)
*G16H 10/60* (2018.01)
*G06Q 40/08* (2012.01)

(52) U.S. Cl.
CPC ......... *G06F 21/6245* (2013.01); *G16H 10/60* (2018.01); *G06Q 40/08* (2013.01)

(58) Field of Classification Search
None
See application file for complete search history.

(56) References Cited

U.S. PATENT DOCUMENTS

| 5,751,287 A | 5/1998 | Hahn et al. |
| 6,640,304 B2 | 10/2003 | Ginter et al. |
| 8,108,311 B2 | 1/2012 | Herlitz |
| 2004/0034550 A1* | 2/2004 | Menschik .............. G06Q 50/24 705/3 |

(Continued)

OTHER PUBLICATIONS

Marshall Brain, Tracy V. Wilson & Bernadette Johnson "How WiFi Works" Apr. 30, 2001. HowStuffWorks.com. <https://computer.howstuffworks.com/wireless-network.htm> Jan. 13, 2020 (Year: 2020).*

*Primary Examiner* — Jacob C. Coppola
*Assistant Examiner* — Jason B Fenstermacher
(74) *Attorney, Agent, or Firm* — Rahman LLC

(57) ABSTRACT

A system for authorizing an external device to access computerized records. The system includes a server. The server includes a computerized records data-store. The computerized records data-store stores multiple computer executable files associated with subjects. The system includes a communication network which facilitates communication between at least two of the subjects, the server, and the external device. The system includes a contextual authorization device for authorizing access to the external device for the computerized records. The contextual authorization device includes a database storing a set of custom rules. The contextual authorization device further includes a Global Positioning System-based tracking device, a credentialing engine, and a user behavior analytics engine. The contextual authorization device further includes an access module to process authorization of the external device for access of the computerized records.

6 Claims, 12 Drawing Sheets

(56) References Cited

U.S. PATENT DOCUMENTS

| | | |
|---|---|---|
| 2007/0005397 A1 | 1/2007 | Lee |
| 2008/0014931 A1 | 1/2008 | Yared et al. |
| 2009/0172795 A1 | 7/2009 | Ritari et al. |
| 2010/0070448 A1 | 3/2010 | Omoigui |
| 2011/0191862 A1* | 8/2011 | Mandava .............. H04L 63/107 726/28 |
| 2012/0245958 A1 | 9/2012 | Lawrence et al. |
| 2013/0047233 A1* | 2/2013 | Fisk ........................ H04L 63/18 726/7 |
| 2015/0046192 A1* | 2/2015 | Raduchel ................ G06F 19/00 705/3 |
| 2016/0050208 A1* | 2/2016 | Arasavelli ............. H04L 63/105 726/29 |

* cited by examiner

FIG. 5

| 502 | 504 | 506 | 508 | 510 | 512 |

ENTER PATIENT NAME
ENTER PATIENT CODE
RECORD TYPE
DATE RANGE FOR RECORD
PATIENT AUTHORIZATION CODE
BANK ACCOUNT DETAILS

CREATE RECORD
514

500

SELF-CONTROLLED DIGITAL AUTHORIZATION OVER COMMUNICATION NETWORKS

CROSS-REFERENCE TO RELATED APPLICATIONS

This application is a continuation-in-part of U.S. patent application Ser. No. 13/607,997 filed on Sep. 10, 2012, the complete disclosure of which, in its entirety, is hereby incorporated by reference.

BACKGROUND

Technical Field

The embodiments herein generally relate to electronic records systems, and, more particularly, to storage, access and authorization of electronic records for access over a communication network.

Description of the Related Art

Generally, several types of services such as financial services, healthcare services or information services or others, and associated parameters, attributes and responses related to the services are documented by entities such as physicians, doctors, hospitals or other service providers, analysts, specialists, and others dealing in information management. At times, information holders or owners such as patients may also document their information or data. With the advent of new technologies, such types of documented information can be stored electronically which is generally referred to as electronic records.

Electronic records are user or owner specific and are generally kept as confidential by the owner of the information or the records. In modern days, these records can be deposited and secured in a central database that is connected over a networked platform such as through an internet that can be accessible by the owner easily.

In certain conditions, an external device other than the patient such as a general consumer of the information or records may be interested in the electronic records and may want to access them. However, as per the conditions prescribed by several authorities and standards such as the Health Insurance Portability and Accountability Act (HIPPA) meant for health-related information and several others, it is imperative and important to gain authorization from an owner for accessing his electronic records. The process of authorization can be fairly simple if the records are limited. An external device or a consumer may directly approach the owner for authorization. However, as the data contained within the records increase to a large extent, the task of identifying relevant data and gaining access and authorization becomes complex and difficult.

SUMMARY

The embodiments herein provide a distributed architecture-based system for digitally authorizing access to computerized records. The system includes at least one server. The server includes at least one computerized records datastore storing multiple computer executable files associated with a subject and containing subject data in a digital format and associated with a subject identifier that identifies association of the subject with its respective computer executable file. The system includes an external device communicatively linked to the at least one server. The system includes a scanner operatively linked to the external device. The system includes a communication network communicatively linking at least two of the subject, the server, the external device, and the scanner.

The system includes a contextual authorization device for authorizing access to the external device. The contextual authorization device includes a database storing a set of custom rules digitally dictating access rights and levels for the external device based on static information associated with the external device and based on dynamically changing contextual information. The contextual authorization device further includes a Global Positioning System (GPS)-based tracking device for tracking a geo-location of the external device such that the custom rules define different rights for different location types as identified from the geo-location of the external device. The different rights define either one of an outright denial or approval of the access or limiting the access to one or more types of digital records based on the location types. The contextual authorization device further includes a credentialing engine to determine a crowdsourced credentialing score associated with an entity associated with the external device. The crowdsourced credentialing score is determined based on credentialing of a digital profile of the entity by a plurality of respondents such that the crowdsourced credentialing score is indicative of a trust of the external device. The custom rules are defined to allow authorization of the external device only when the entity associated with the external device possesses at least a minimum threshold score. The contextual authorization device further includes a user behavior analytics engine to compare dynamically changing contextual details associated with the entity with a set of past requests indicative of historical behavior and determine an index of normality such that the custom rules are defined to allow the access only when a minimum predefined threshold of normality is noted about the external device and the associated entity.

The contextual authorization device further includes an access module that processes authorization of the external device for access of the computerized records based on an input received from the GPS-based tracking device, credentialing engine, and the user behavior analytics engine. The contextual authorization device further includes a processing component that creates the computerized records based on the authorization by the access module. The processing component transforms the authorized computerized records into a digital data structure readable by the scanner.

The system may include an interface unit for providing a graphical user interface to the subject and the external entity associated with the external device to respectively update the computerized records of the subject and view or extract the computerized records as authorized by the contextual authorization device. The system may include a communication channel allowing transfer of the computerized records through at least one of a wired and wireless transmission technique to a destination identified by the external device, upon successful authorization of the access by the contextual authorization device. The system may include an input module configured to receive binary values relating authorization access such that the custom rules may be used in association with the input for providing access to the external device by the contextual authorization device. The contextual authorization device may be configured to select a real time automated manner of access authorization for the computerized records based on the custom rules stored in the database.

The system may include a document usage system which may include one or more document computer systems in communication with a network of devices including the external device and having a machine-accessible medium storing a plurality of program modules configured to determine document utilization information providing an indication of usage of computerized records as authorized to be accessed by the external device associated with the entity. The usage comprises an amount of time that the associated entity or the external devices has accessed particular sections of the authorized computerized records. The computerized records may be classified into discrete types. The system may include a monetization engine configured to associate a price value with the authorized computerized records based on the usage by the external device and based on the classification of authorized computerized records as accessed by the external device are classified into. The digital data structure may include a QR (quick response) code readable by the scanner.

The embodiments herein provide a portable device for encapsulating computerized records of multiple types. The portable device includes a plurality of memory segments, wherein each of the plurality of memory segments stores a specified type of computerized records and is accessible by an external device upon successful authorization. The portable device includes an access module that processes authorization to access the computerized records by the external device based on certain inputs received from external components to the portable device. The portable device includes a processing component that creates the computerized records based on the authorization by the access module, wherein the processing component transforms the authorized computerized records into a digital data structure readable by a scanner communicatively connected with the external device.

The portable device is communicatively connected with a remote server. The remote server includes a contextual authorization device for generating the certain inputs for use by the access module in authorizing access to the external device for the computerized records. The contextual authorization device includes a database storing a set of custom rules digitally dictating access rights and levels for the external device based on static information associated with the external device and based on dynamically changing contextual information. The contextual authorization device includes a Global Positioning System (GPS)-based tracking device for tracking geo-location of the external device such that the custom rules define different rights for different location types as identified from the geo-location of the external device. The different rights define either one of an outright denial or approval of the access or limiting the access to one or more types of computerized records based on the location types. The portable device includes a user interface with a plurality of single-click configurable menu options defined to provide authorization request in a single click such that a single-click configurable menu option of the plurality of single-click configurable menu options is defined to authenticate only a particular type of computerized record with a particular level of access. The level of access includes one of a full access, limited access, and no access, wherein the level of access is defined based on geo-location of the external system and the portable device.

The portable device includes a communication terminal configured to establish a communication link between the portable device and the external device as soon as any of the plurality of single-click configurable menu options is pressed by a user. The access module is allowed to authorize the access of the computerized records either based on the certain inputs received from the remote server without any manual intervention or alternatively based on single click manual authorization using one of the plurality of single-click configurable menu options to allow access of the computerized records of a particular type defined for a particular context.

The contextual authorization device may include a credentialing engine to determine a crowdsourced credentialing score associated with an entity associated with the external device. The crowdsourced credentialing score may be determined based on credentialing of a digital profile of the entity by a plurality of respondents such that the crowdsourced credentialing score is indicative of a trust of the external device. The custom rules may be defined to allow authorization of the external device only when the entity associated with the external device possesses at least a minimum threshold score. The contextual authorization device may include a user behavior analytics engine to compare dynamically changing contextual details associated with the entity with a set of past requests indicative of historical behavior and determine an index of normality such that the custom rules may be defined to allow the access only when a minimum predefined threshold of normality is noted about the external device and the associated entity.

The communication terminal may be a near-field communication (NFC) terminal with one or more NFC taps configured to establish a communication link between the portable device and the external device as soon as any of the plurality of single-click configurable menu options is pressed by a user and the one or more NFC taps is activated. The communication terminal may be a WiFi hotspot with one or more WiFi taps configured to establish a communication link between the portable device and the external device as soon as any of the plurality of single-click configurable menu options is pressed by a user and the one or more WiFi taps is activated. The plurality of single-click configurable menu options may include a single-click configurable option for a hospital terminal computer, a single-click configurable option for a pharmacy terminal computer, a single-click configurable option for a lab terminal computer such that each of the plurality of single-click configurable options may be defined by respective location types associated with particular levels of access to particular types of computerized records as defined through associated geo-locations. The external device may include a mobile computing device associated with the entity and may be configured to process a request to access the computerized records. The external device may include a swipe machine configured to receive a portion of the integrated chip such that the scanner may include a swipe machine reader configured to read the integrated chip for extracting the computerized records according to authorization by the authorization module. The digital data structure may include a QR (quick response) code readable by the scanner. The portable device may further include a printed circuit board mounting the plurality of memory segments, the processing component, and electrical circuitry. The portable device may include a housing component for encapsulating the printed circuit board, and a battery for providing a power source for the portable device.

BRIEF DESCRIPTION OF THE DRAWINGS

The embodiments herein will be better understood from the following detailed description with reference to the drawings, in which:

FIG. 5 illustrates generally, but not by way of limitation, an example of an interface providing a capability to the external device such as to access the server for requesting the authorization to access or create the computerized records, at least in part, stored at the server according to the embodiments herein;

DETAILED DESCRIPTION

Figure 1:
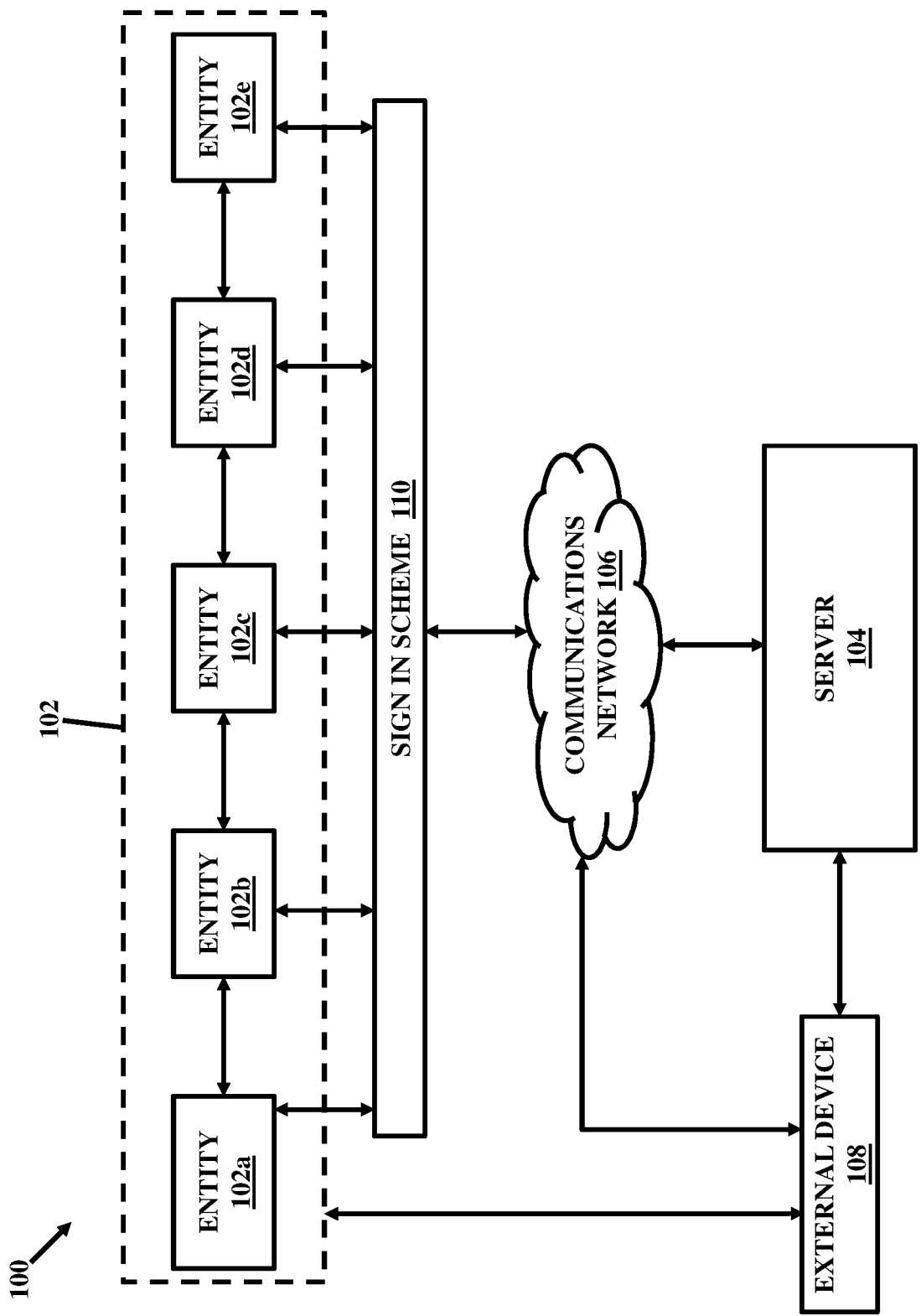
FIG. 1 illustrates generally, but not by way of limitation, among other things, an example of an environment or architecture in which various embodiments herein may operate.

The embodiments herein and the various features and advantageous details thereof are explained more fully with reference to the non-limiting embodiments that are illustrated in the accompanying drawings and detailed in the following description. Descriptions of well-known components and are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

In the following detailed description, reference is made to the accompanying drawings that form a part hereof, and these are shown by way of illustrating specific embodiments herein that may be practiced. These embodiments, which are also referred to herein as "examples," are described in sufficient detail to enable those skilled in the art to practice the embodiments herein, and it is to be understood that the embodiments may be combined, or that other embodiments may be utilized and that structural, logical, and electrical changes may be made without departing from the scope of the embodiments herein.

In this document, the terms "a" or "an" are used, as is common in patent documents, to include one or more than one. In this document, the term "or" is used to refer to a "nonexclusive or" unless otherwise indicated.

In an exemplary embodiment, the various modules described herein and illustrated in the figures are embodied as hardware-enabled modules and may be configured as a plurality of overlapping or independent electronic circuits, devices, and discrete elements packaged onto a circuit board to provide data and signal processing functionality within a computer. An example might be a comparator, inverter, or flip-flop, which could include a plurality of transistors and other supporting devices and circuit elements. The modules that are configured with electronic circuits process computer logic instructions capable of providing digital and/or analog signals for performing various functions as described herein. The various functions can further be embodied and physically saved as any of data structures, data paths, data objects, data object models, object files, and database components. For example, the data objects could be configured as a digital packet of structured data. The data structures could be configured as any of an array, tuple, map, union, variant, graph, tree, node, and an object, which may be stored and retrieved by computer memory and may be managed by processors, compilers, and other computer hardware components. The data paths can be configured as part of a computer CPU that performs operations and calculations as instructed by the computer logic instructions. The data paths could include digital electronic circuits, multipliers, registers, and buses capable of performing data processing operations and arithmetic operations (e.g., Add, Subtract, etc.), bitwise logical operations (AND, OR, XOR, etc.), bit shift operations (e.g., arithmetic, logical, rotate, etc.), complex operations (e.g., using single clock calculations, sequential calculations, iterative calculations, etc.). The data objects may be configured as physical locations in computer memory and can be a variable, a data structure, or a function. In the embodiments configured as relational databases (e.g., such Oracle® relational databases), the data objects can be configured as a table or column. Other configurations include specialized objects, distributed objects, object oriented programming objects, and semantic web objects, for example. The data object models can be configured as an application programming interface for creating HyperText Markup Language (HTML) and Extensible Markup Language (XML) electronic documents. The models can be further configured as any of a tree, graph, container, list, map, queue, set, stack, and variations thereof. The data object files are created by compilers and assemblers and contain generated binary code and data for a source file. The database components can include any of tables, indexes, views, stored procedures, triggers.

FIG. 1 illustrates generally, but not by way of limitation, among other things, an example of an environment or architecture 100 in which various embodiments herein may operate. As illustrated in FIG. 1, the environment 100 constitutes a plurality of entities 102a, 102b, 102c, 102d, and 102e, together referred to as 102, communicatively in connection with a server 104 over a network 106.

In embodiments, the entities 102 may include patients (also referred to as subject interchangeably), financial professionals, experts of various domains, researchers, scholars, students, or any other person who maintains records related to specific tasks. The entities 102, as described herein, generally maintain records more specifically in the form of electronic forms referred to as electronic records. The entities 102 may be connected communicatively with one another and also with the server 104.

The server 104 is configured as a central database or repository for managing and storing the electronic records of the entities 102. In accordance with various embodiments, the server 104 stores the electronic records that are submitted by the entities 102. These records may include such as financial records, medical or health records, scientific records, literary work, intellectual property or copyrighted material, personal records, and the like, without limitations. In an embodiment, the server 104 may be configured as a distributed database with multiple access points for storing and accessing the electronic records of the entities 102 in a distributed manner configured through a blockchain enabled network.

As shown, the architecture 100 also includes an external device 108 which may be communicatively connected with the entities 102 and/or the server 104 over the network 106. The external device 108 may serve as a customer who may desire to access the electronic records, at least in part. In embodiments, the external device 108 may be associated with a patient, financial service provider such as an insurance company, healthcare professional or healthcare service provider, and the like.

The entities 102 can be communicatively connected with the server 104 by such as registering with the server 104. The entities 102 can register, in an embodiment, through a sign in scheme 110. The sign in scheme 110 can facilitate as a networking platform or portal for configuring communication among the entities 102 and also between the entities 102 and the server 104. Also, the sign in scheme 110 can communicatively connect the entities 102 and the server 104 with the external device 108. In an embodiment, the sign in scheme 110 can be established with the use of a networked portal. In an embodiment, the sign in scheme 110 can be established with the use of such as a social networking platform.

The network 106 can be a wireless or a wired network. The network 106 can operate as a communications network configuring communication among the entities 102, the server 104, and the external device 108. In an embodiment, the network 106 can be an internet. The entities 102, the server 104, and the external device 108 can be distributed over a wide area and can connect remotely among themselves over the network 106 which may be a blockchain configured network, in some embodiments.

Figure 2:
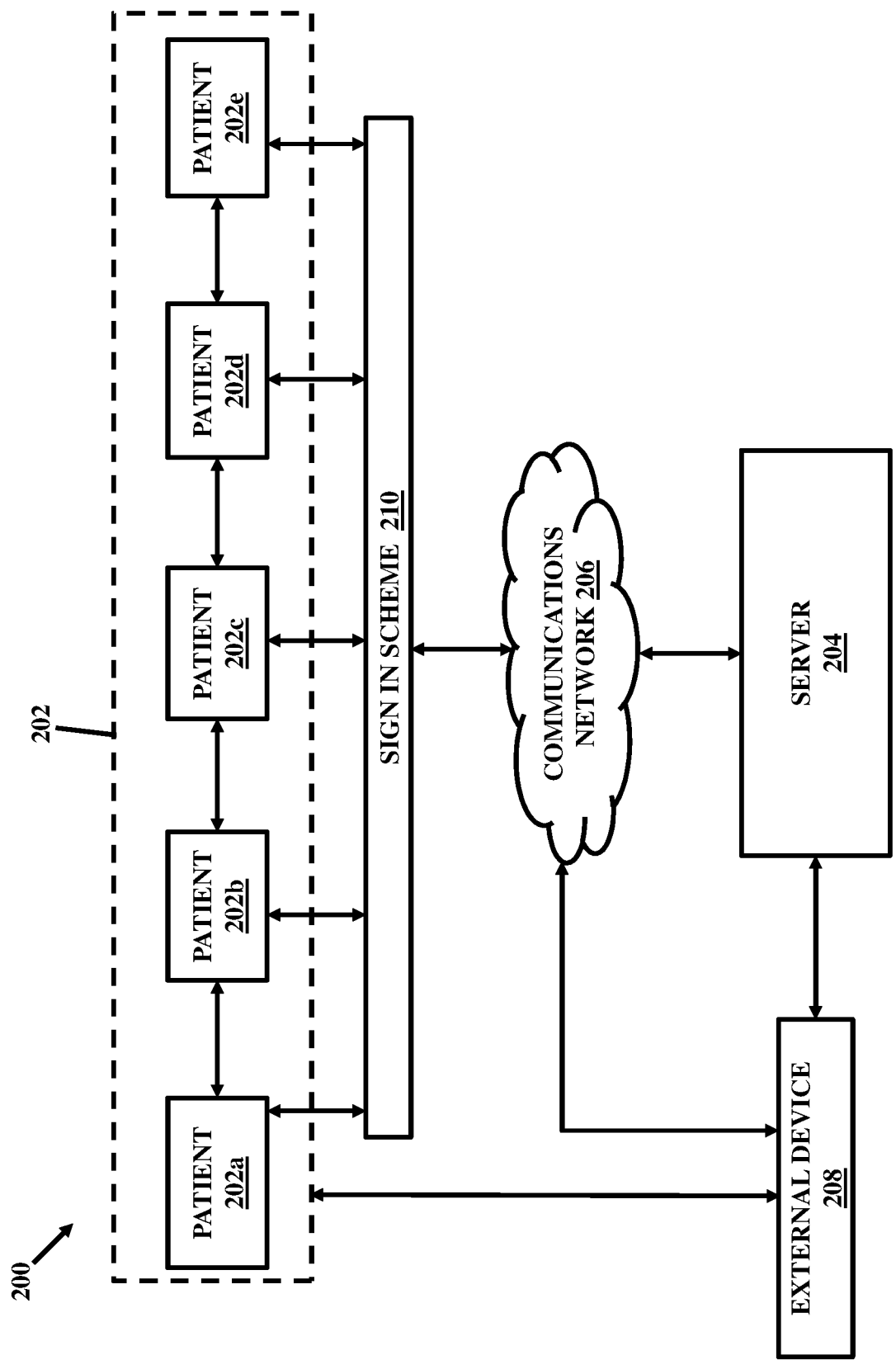
FIG. 2 illustrates generally, but not by way of limitation, among other things, a specific example of an environment or architecture in which at least some embodiments herein may operate.

FIG. 2, with reference to FIG. 1, illustrates generally, but not by way of limitation, among other things, a specific example of an environment or architecture 200 in which at least some embodiments of the present invention may operate. As illustrated in FIG. 2, the environment constitutes a plurality of patients 202a, 202b, 202c, 202d, and 202e (together referred to as 202 hereinafter, also referred to subjects interchangeably) communicatively in connection with a server 204 over a network 206. The patients 202 can be communicatively connected with the server 204 through respective computing devices by such as registering with the server 204. The patients 202 can register, in an embodiment, through a sign in scheme 210 which is similar to the sign in scheme 110 as described with respect to FIG. 1.

As shown, the architecture 200 also includes an external device 208 which may be communicatively connected with the patients 202 (or associated respective computing devices) or through the server 204 over the network 206. The external device 208 may serve as a customer device which may request to access the electronic records, at least in part. In embodiments, the external device 208 may be associated with a patient, healthcare professional or healthcare service provider, and the like. It should be appreciated that FIG. 2 illustrates an exemplary environment applicable for creating or storing or managing or authorizing digital access for electronic records in a typical medical or healthcare environment, however the embodiments herein are equally applicable to other environments such as those generically recited and discussed without limitations in conjunction with FIG. 1.

Referring now to FIGS. 3 through 8, the embodiments herein are discussed in conjunction with the environment 200 discussed in FIG. 2, as an exemplary embodiment.

Figure 3:
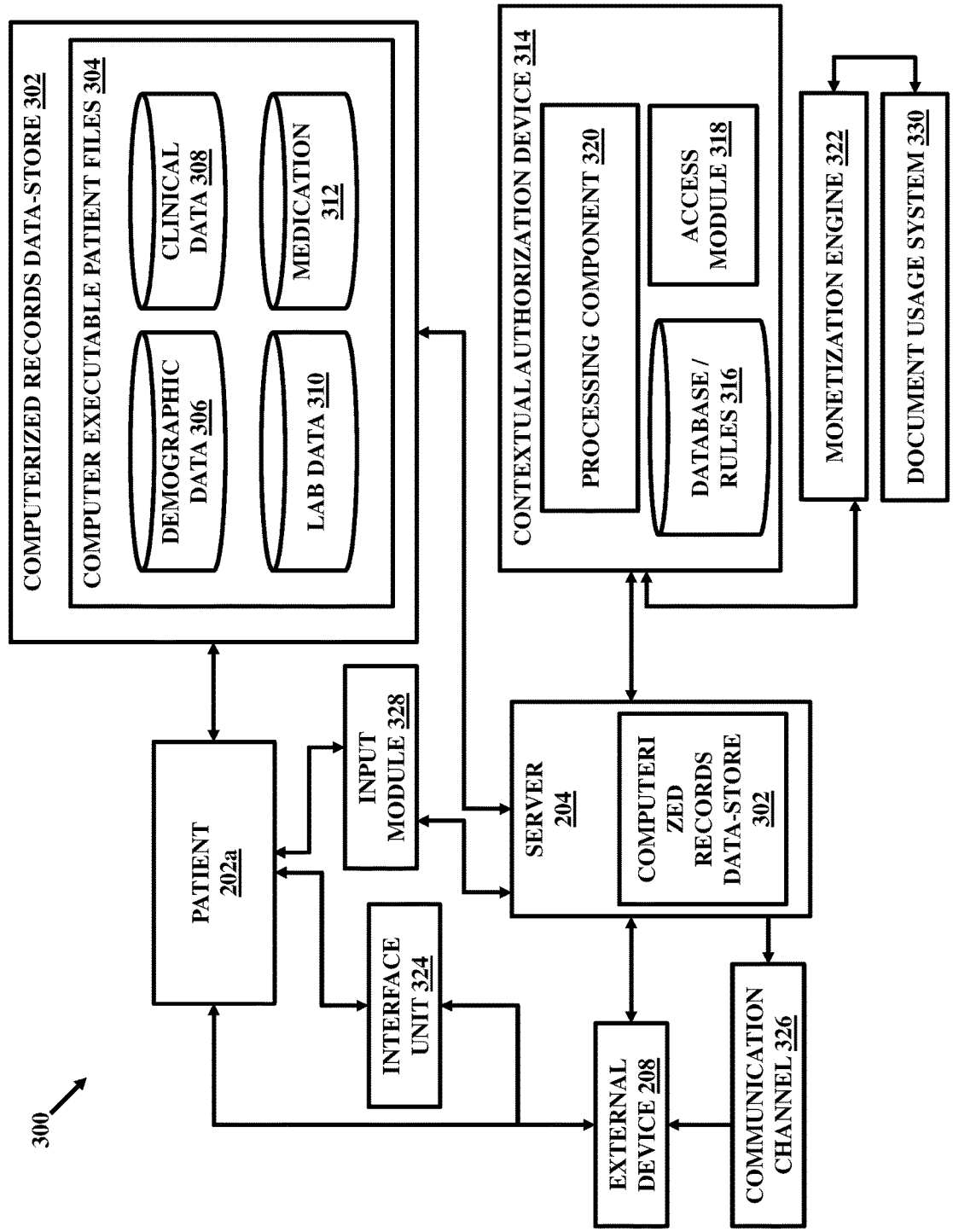
FIG. 3 illustrates a system for storing and creating computerized records, and authorizing access to an external device, at least in part, for the computerized records according to the embodiments herein.

FIG. 3, with reference to FIGS. 1 through 2, illustrates a system 300 connected to a patient 202a for storing and creating computerized records (also referred to as electronic records or digital records interchangeably), and authorizing access to the external device 208, at least in part, for the computerized records. As shown, the system 300 includes at least one server similar to the server 204. The server 204 includes or is coupled to at least one computerized records data-store 302. In an embodiment, the computerized records data-store 302 can be a central database. In an embodiment, computerized records data-store 302 can be a distributed blockchain enabled data store with distributed access points. The at least one computerized records data-store 302 stores multiple computer executable patient files 304. Each computer executable patient file is associated with a patient such as the patient 202a and contains patient data. The patient 202a is registered with the at least one computerized records data-store 302 via the sign in scheme 210 and allowed to store the computerized records associated with the patient 202a after signing in through the sign in scheme 210. In an embodiment, the information submitted and stored by the patient 202a in the server 204 can be collated together to define a sub-database specific for the patient 202a that can be referred to as a computer executable patient file. Similarly, several patients storing information for various patients constitute what is termed here as the computer executable patient files 304. The computer executable patient files 304 may include patient information or patient data of a variety of types stored in a digital format. For example, in an embodiment, the information or data may include at least one of demographic data 306, clinical data 308, lab data 310, medication related data 312, and the like without limitations stored in a digital format. In an embodiment, the patient data may include the medical history of the patient 202a such that the computer executable patient file may define the medical history of the patient 202a. In an embodiment, critical patient information is stored in the computer executable patient files such that the computer executable patient files define critical patient information for the patient 202a.

As discussed in conjunction with FIGS. 1 and 2, the patient 202a can store the data or computer executable patient files in the server 204 upon registering with the server 204 through such as the sign in scheme 210 enabled through such as an internet based platform. The internet based platform can be a social networking platform, in an embodiment. In an embodiment, the patient 202a can access the server 204 for registration through his/her personal login details configured for accessing such as his/her social networking platform or internet based emailing platforms. In another embodiment, the patient 202a, upon signing in through the sign in scheme 210 may be directed to an altogether separate interface linked to such as his/her social networking platform. The interface, in such cases, may generate fresh credentials for accessing the server 204 through such as his/her social networking platforms.

In an embodiment, information indicative of a patient interest in selling or authorizing access for the computerized records, at least in part, is viewable publicly to the external device 208 upon registration of the patient 202a with the computerized records data-store 302.

The system 300 further includes the communication network 206 (shown in FIG. 2) such that the system 300 is connected over the communication network 206. The network 206 further facilitates communication between the patient 202a and the external device 208. In an embodiment, the external device 208 can access the server 204 upon registration in a manner similar to that described above with respect to the patients 202. In other embodiments, several other ways of access may also be possible such as gaining a subscription for a dedicated interface that links the external device 208 to the server 204 and its data stored therein. However, access to the digital data or information stored on the server 204 such as the computer executable patient files 304, either in part or in entirety, is conditional subject to authorization from the patient 202a associated with the respective computer executable patient files 304 and may be accessed only upon successful authorization and payment for the access.

The system 300 further includes a contextual authorization device 314 for authorizing access to the external device 208 for the computerized records, at least in part. The contextual authorization device 314 includes a database 316 that stores a set of rules dictating access rights and levels for the external device 208 based on information associated with the external device 208 and/or associated entity. In an embodiment, the set of rules are defined by the patient 202a based on such as a role of the external device 208, scope of authorization, nature of access, nature or purpose of usage of the computerized records, payments associated in return of the access, type of information such as demographic, lab data, medication related, and the like. In an embodiment, specific types of information may be defined by unique identifiers such as for example demographic information of the patient 202a may be defined by a first identifier, clinical information of the patient 202a may be defined by a second identifier, lab information of the patient 202a may be defined by a third identifier, and medication related information may be defined by a fourth identifier. The set of rules as defined by the patients 202a may be associated with specific identifiers so as to cumulatively define rules based on the nature of the information. Thus, the set of rules may vary as the nature of information varies. Similarly, the set of rules may also define payment options and payment requirements which may also be associated in conjunction with the identifiers for the specific information. Therefore, payment requirements for example for the demographic information may be different from the payment requirements of the clinical information. In an embodiment, the patient 202a may also place restrictions for accessing more complicated, important and critical information such as medication related information as compared to relatively less critical information such as demographic information. Accordingly, the external device 208 may be required to justify its access such as by producing valid documents highlighting importance and genuineness of the access. Also, in such cases, the payment requirements may be higher relatively as defined by the set of rules in association with a respective identifier. In general, the set of rules are defined to govern access of the external device 208 and validate the access by the patient 202a.

The contextual authorization device 314 further includes an access module 318 that processes authorization of the external device 208 for access of the computerized records, at least in part. In an embodiment, the authorization is processed by using an output generated by the access module 318 based on the set of rules, information received from the external device 208 defining nature of the external device 208, purpose of the access, and scope of access, and the like. The access module 318 receives detailed quantitative and/or qualitative information from the external device 208 before providing authorization. The access module 318 is coupled to the central database 316 and is configured to accesses the set of rules stored therein and map the received information from the external device 208 onto the set of rules. Upon mapping, the access module generates an output that decides a grant or denial of authorization for the medical records specific to the patient 202a and also a level of access such as limited access or full access to one or more types of records.

The contextual authorization device 314 further includes a processing component 320 that creates or extracts the computerized records, at least in part, based on the authorization by the access module 318. The processing component 320 receives an input from the access module 318 and accordingly configures and issues a command to extract the requested computerized records and email them to the external device 208 or save at a defined location for access by the external device 208, or give direct access rights to the external device 208 or sends a print command for issuing hard copies thereof.

In an embodiment, the contextual authorization device 314 may be coupled to a monetization engine 322 that is configured to associate a numerical value to the request of the external device 208 for gaining authorization to the computerized records, at least in part, as requested by the external device 208. The numerical value defines a billable amount to be paid by the external device 208 in return of the authorization grant for the computerized records, at least in part. In an embodiment, price standards can be defined by the patient 202a in association with specific types of the information that are defined by their respective identifiers. The price standards can be stored as a part of the set of rules or can also be stored and considered separately. The monetization engine 322 can associate the price standards such as based on the set of rules with the information received from the external device 208 specifying such as nature and role of the external device 208, purpose of the access, and scope of the access, time of usage of the computerized records, and with the type of information such as defined by the identifiers. For example, a specific combination of the information received from the external device 208 and the demographic information for a specific role of the external device 208 and for a specific purpose and scope of access may yield a price value different from another combination for the same external device 208 but with different purpose and scope of the access and for different information such as lab data or clinical information. In an embodiment, the monetization engine 322 may operate based on certain defined algorithms that operate hardware elements of the monetization engine 322 to function for calculation purposes resulting in an output in the form of a numerical value that can be associated with the request for authorization as its billable charge. The concept as defined by the monetization engine 322 in association with other concepts of the invention allows the patient 202a and other patients such as 202 to be paid for their computerized records such as by the external device 208 who requests to gain or gains access for them or buys or requests to buy or gains license or requests to gain license, at least in part. The pay as you buy or pay as you access concept facilitate to set up a marketplace enabled through the network 206 such as through the Internet for open selling, purchasing and licensing of medical records. In an embodiment, the monetization engine 322 may include or be coupled to a document usage system 330. The document usage system 330 may include one or more document computer systems in communication with a network of devices including the external device 208 and having a machine-accessible medium storing a plurality of program modules configured to determine document utilization information providing an indication of usage of computerized records at least in part as authorized to be accessed by the external device 208 associated with the entity. The usage may include an amount of time for which the associated entity or the external device 208 accesses particular sections of the authorized computerized records. The monetization engine 322 may calculate price value for billing to the external system based on the usage of the computerized records, at least in part. In an embodiment, the computerized records may be classified into discrete types and the monetization engine 322 may be configured to associate a price value with the authorized computerized records based on the usage by the external device 208 based on the type the authorized computerized records as accessed by the external device 208 are classified into.

In an embodiment, the system 300 may include an interface unit 324 for providing an interface to the patient 202a and the external device 208 to respectively update the patient's computerized records by the patient 202a and view or extract the computerized records by the external device 208 as authorized by the patient 202a, at least in part.

The system 300 may include a communication channel 326 allowing transfer of the computerized records through at least one of a wired and wireless transmission technique to a destination identified by the external device 208, upon successful authorization of the access by the patient 202a and payment of a billable amount equivalent to obtain the access right of the computerized records, at least in part, as specified by the patient 202.

In an embodiment, the system 300 further includes an input module 328 to receive an input manually from the patient 202a regarding authorization access in terms of binary values and costs associated with the authorization access. The binary values may represent as YES or NO representing grant or denial of the access respectively to the external device 208 for a specific request manually. In an embodiment, the set of rules can be used in association with the input received manually from the patient 202a for providing access to the external device 208. In accordance with various scenarios, the patient 202a can be allowed to alternatively select one of the below two options for authorization:

The first option may include an automated way of access authorization for the computerized records, at least in part, based on the set of rules stored in the database 316.

The second option includes a manual way of access authorization for the computerized records, at least in part, based on the input received by the patient 202a manually through the input module 328.

In an embodiment, the external device 208 can also be communicatively connected to the patient 202a through such as the social networking platform or any other networked platform through the sign in scheme 210.

In an embodiment, the server 204 can be maintained by a service provider of a social networking service such that the server 204 is one of several repositories maintained by the provider of the social networking service through the social networking platform.

In accordance with an embodiment, the system 300 is described with respect to computerized records. However, it must be appreciated that the system 300 can be employed in other scenarios also within the scope of the embodiments herein. For example, in an embodiment, the system 300 can be used for storing and creating computerized records including but limited to medical records, financial records, scientific literature, art and literature, and the like and for authorizing access to a consumer (similar to the external device 208) at least in part for the computerized records by an owner/user similar to the patient 202a of the computerized records. The system 300 includes the at least one server 204 that includes or is coupled to the at least one computerized records data store 302. The at least one computerized records data store 302 stores multiple computer executable files similar to files 304. Each computer executable file is associated with an owner of the computerized records and contain data specific to the owner. The owner is registered with the at least one computerized records data store 302 through the sign in scheme 210 and allowed to store the computerized records associated with the owner after signing in through the sign in scheme 210.

The system 300 includes the communication network 206 such that the system 300 is connected over the communication network 206 and the network 206 facilitates communication between the owner and the consumer. The system 300 further includes the contextual authorization device 314 for authorizing access to the consumer for the computerized records at least in part. The contextual authorization device 314 includes the database 316 storing the set of rules dictating access rights and levels for the consumer based on information associated with the consumer. The contextual authorization device 314 also includes the access module 318 that processes authorization of the consumer for access of the computerized records, at least in part. The contextual authorization device 314 further includes the processing component 320 that creates the computerized records, at least in part, based on the authorization by the access module 318.

Figure 4:
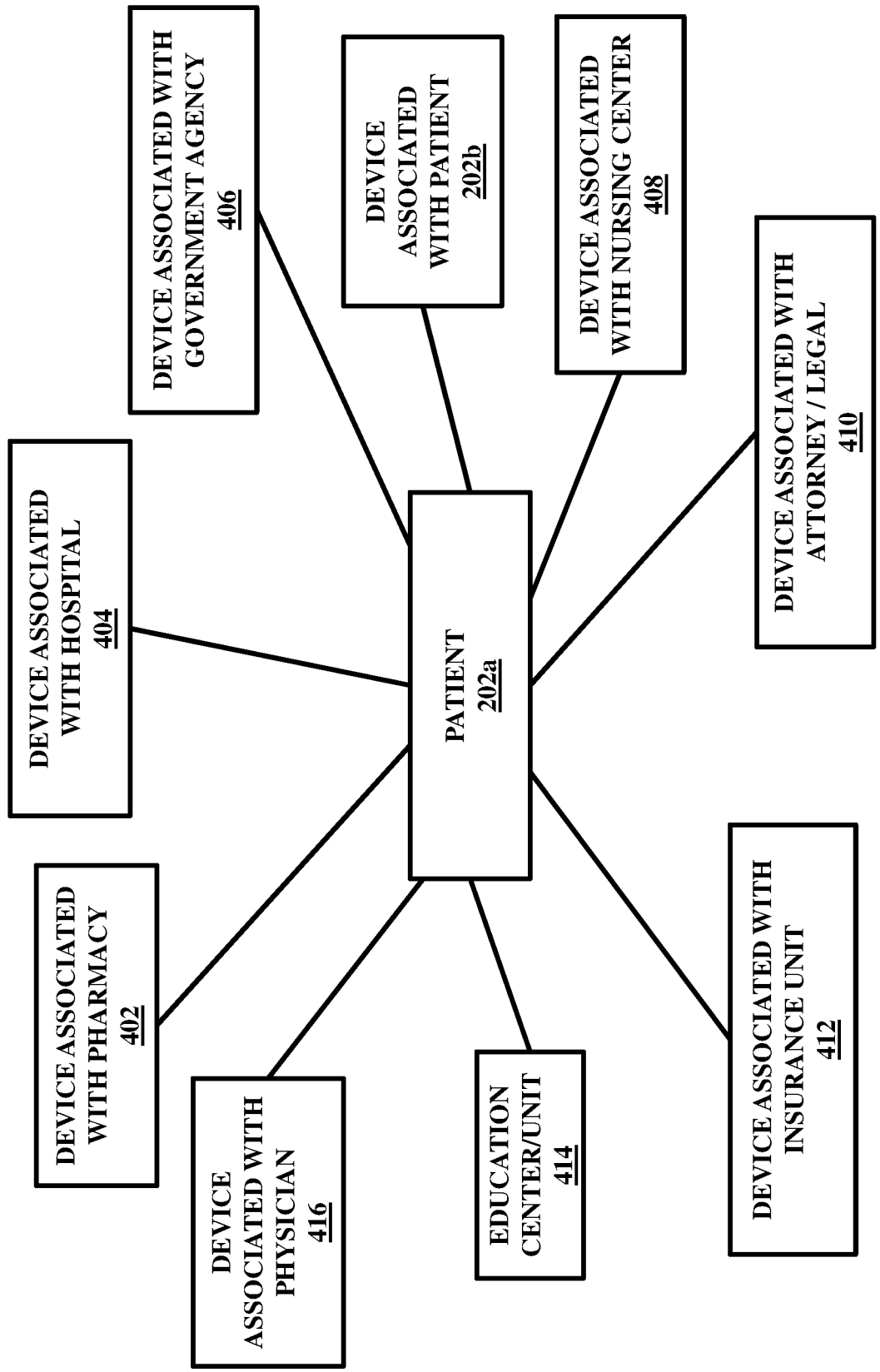
FIG. 4 illustrates a network of several devices representing as similar to the external device that are connected with a subject according to the embodiments herein.

FIG. 4, with reference to FIGS. 1 through 3, illustrates a network of several devices representing as similar to the external device 208 and hereafter referred to as third-party devices, in combination, that are connected with the patient 202a as discussed above via the server 204. In accordance with some embodiments, the external device 208, as shown, can be a mobile device or computer terminal associated with a pharmacy 402, a mobile device or computer terminal associated with a hospital 404, a mobile device or computer terminal associated with a government agency 406, a mobile device or computer terminal associated with another patient 202b different from the patient 202a, a mobile device or computer terminal associated with a nursing center 408, a mobile device or computer terminal associated with an attorney or a legal department 410, a mobile device or computer terminal associated with an insurance unit 412, a mobile device or computer terminal associated with an education center 414, a mobile device or computer terminal associated with a physician 416, and the like, without limitations. As understood from the general meaning of various third-party devices shown in FIG. 4, the roles and purposes of the third-party devices may vary.

FIG. 5, with reference to FIGS. 1 through 4, illustrates generally, but not by way of limitation, an example of an interface 500 providing a capability to the external device 208 such as to access the server 204 for requesting the authorization to access or create the computerized records, at least in part, stored at the server 204, in an embodiment.

The interface 500, as shown in FIG. 5, can be accessed such as through a credential provided to the external device 208 and including a login identifier and a unique personal password. The interface 500 can include such as a tab 502 for entering the patient name whose computerized records are required to be accessed. The interface 500 can also include a tab 504 for entering a patient code specific for the patient 202a whose computerized records are required to be accessed. The external device 208 can also filter the requested access by providing details of the nature of information requested such as demographic, clinical, medication, lab report and the like through another record type tab 506 facilitated on the interface 500. The interface 500 can also include graphical user interfaces (GUIs) such as a tab 508 for entering date limitations for the records to be accessed. It must be appreciated that some or all of the above tabs may be replaced by other tabs, in accordance with other embodiments, as per requirements without limiting the scope of the invention. For example, instead of the tabs for patient name and patient code, a searchable interface may be provided that can be configured to search for patients relevant for a specific type of medical information. The searchable interface can automatically search and generate names and codes of relevant patients which can be short-listed by the external device 208. Similarly, several other modifications in the tabs and the interface 500 can be made within the scope of the embodiments herein.

In addition, the tabs as discussed above, and the interface 500 may include one or several tabs to identify banking, financial, and payment related details of the external device such as to launch a financial transaction. As an example shown in FIG. 5, the interface 500 includes a tab 512 referred to as bank account details which may be used to provide bank details or other financial details such as credit card number, debit card number, bank account number, and bank name and branch, and the like. The grant of authorization may also depend on the verification of the bank account details along with several other details. The verification can be done by linking the interface 500 with the respective bank through a secured internet portal.

Before requesting for the authorization, the external device 208 is required to be authorized for the access by the respective patient 202a who holds rights of the requested computerized records. The external device 208 can connect with the patient 202a through the interface 500 so as to get authorization. Upon patient authorization, the external device 208 receives a patient authorization code which may be required to be submitted through the interface 500 along with other details such as through another tab 510 meant for patient authorization code. It must be appreciated that the patient authorization can be completely automated, in an embodiment, such that the request for access can be authorized or denied automatically based on the set of rules stored in the database 316 and based on the information received from the external device 208 such as during submitting of the information through the interface 500. The authorization can also be almost simultaneously processed during the submission of the details through the interface 500. If the authorization is granted, a button 514 meant for such as to create the computerized records is made operable or visible to the external device 208 on the interface 500 for clicking resulting in extraction of the computerized records on a local disk or space, or emailing of the computerized records on a personal email inbox, or retrieval in any other possible manner, upon clicking.

Figure 6:
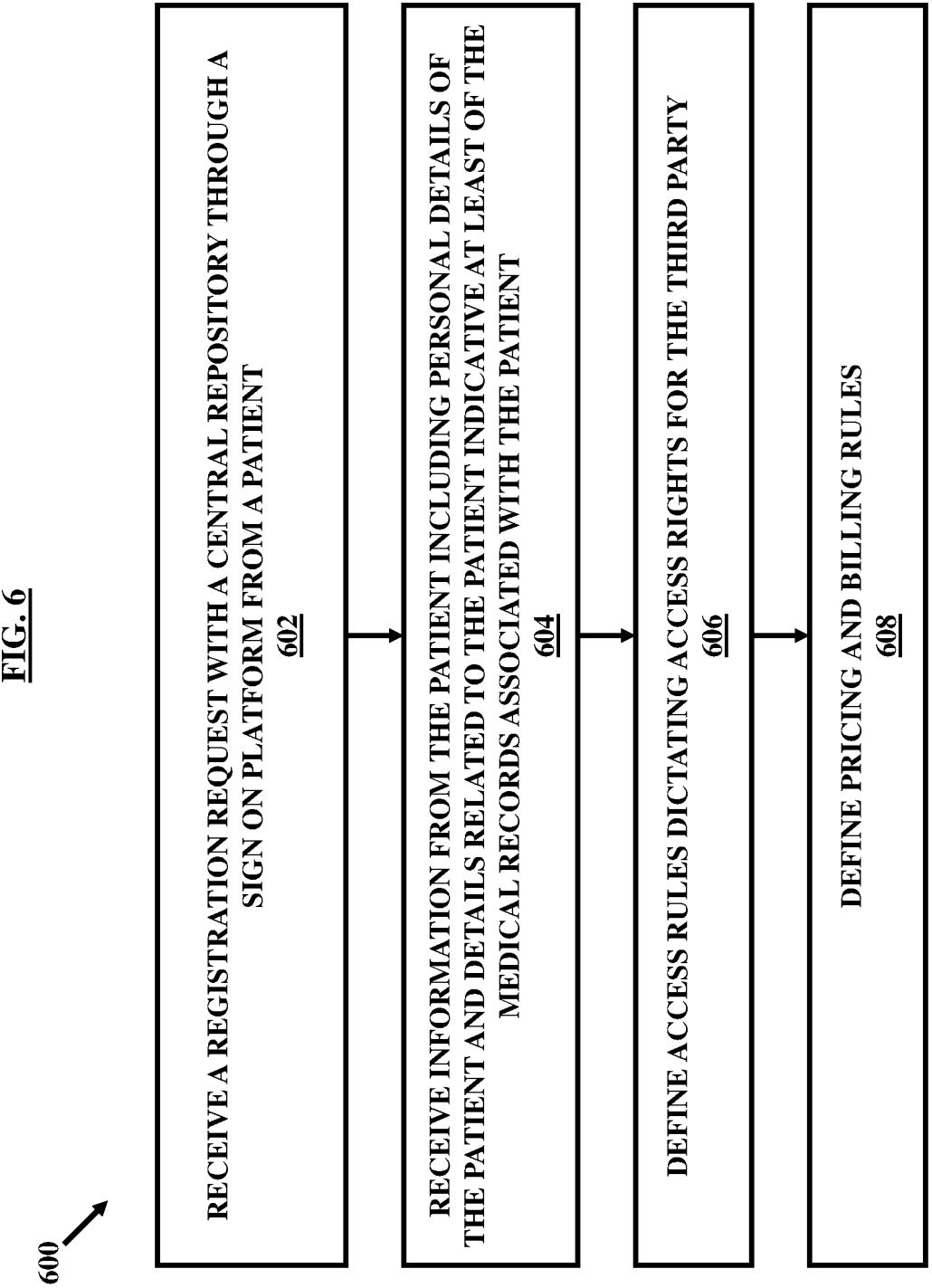
FIG. 6 is a flowchart illustrating a method for sharing the computerized records by the subjects with the server for the purpose of such as authorizing the external device to access the computerized records according to the embodiments herein.

FIG. 6, with reference to FIGS. 1 through 5, illustrates a method 600 for sharing the computerized records by the patients 202 with the server 204 for the purpose of such as authorizing the external device 208 to access the computerized records. At step 602, the method includes receiving a registration request with the computerized records data-store 302 through the sign in scheme 210 from the patient 202a. At step 604, the method 600 includes receiving information from the patient 202a such as including personal details of the patient 202a and details related to the patient 202a indicative at least of the computerized records associated with the patient 202a. The details related to the patient 202a indicative of the computerized records may be the computerized records associated with the patient 202a which are submitted by the patient 202a for storage on the server 204 upon registration and further sharing with others such as the external device 208 later on as per the conditions specified by the patient 202a such as through the set of rules. At step 606, the method 600 includes defining access rules dictating access rights for the external device 208. In an embodiment, the access rules can form a part of the entire set of rules as defined by the patient 202a along with other information such as payment related rules. At step 608, the method 600 includes defining pricing and billing rules or payment related rules. In an embodiment, the access rules and the pricing and billing rules together make up the set of rules. However, in some embodiments, the set of rules may include some more rules governing the access, authorization, and payment and digital data sharing and management other than the access and pricing and billing rules as discussed above.

Figure 7:
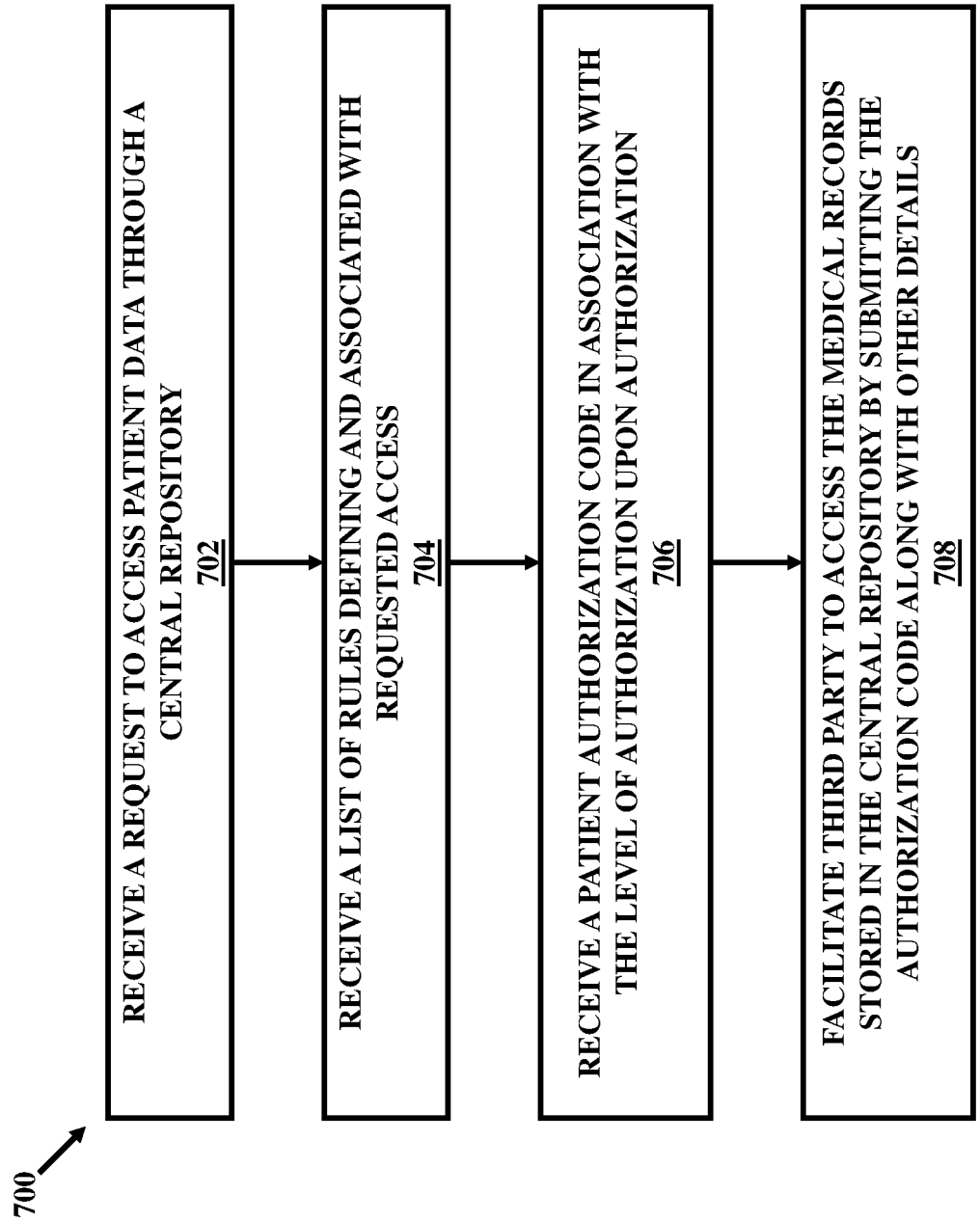
FIG. 7 is a flowchart illustrating a method of granting access or authorizing the external device for the computerized records, at least in part, by the server or the subject according to the embodiments herein.

FIG. 7, with reference to FIGS. 1 through 6, illustrates a method 700 of granting access or authorizing the external device 208 for the computerized records, at least in part, by the server 204 or the patient 202a. At step 702, the method includes receiving the request from the external device 208 to access the patient data or the computerized records associated with the patient 202a through the computerized records data-store 302 of the server 204. At step 704, the method 600 includes receiving a list of rules defining and associated with the requested access. The list of rules is accessed from the database 316 configured to store the set of rules. In an embodiment, the list of rules is a subset of the set of rules and including those rules pertaining to the specific request out of the entire set of rules. In an embodiment, the list of rules can be same as the set of rules. At step 706, the method 700 includes receiving the patient authorization code in association with the level of authorization upon authorization by the patient 202a. In an embodiment, the request first may be redirected to the patient 202a for authorization. In another embodiment, the request may be automatically processed for authorization based on the set of rules defined by the patient 202a. If the authorization results in the grant of the access, the authorization code is generated which is used by the server 204 for allocating rights to access the medical records. On the contrary, if the access is denied, the authorization code is not generated, and the external device 208 is denied or blocked for access. At step 708, in case the authorization is made, the method 700 includes facilitating the external device 208 to access the computerized records stored in the computerized records data-store 302 by submitting the authorization code along with other details. Before final authorization, the external device 208 may be required to clear payments for the access of the computerized records, at least in part.

In an embodiment, the method 700 includes updating the set of rules periodically by the patient 202a, and terminating the access of an already authorized access upon not meeting requirements prescribed by a new set of rules as defined by updating.

The embodiments herein may be related to a single or limited number of patients. However, it should be appreciated that a plurality or a network of the patients 202 (as shown in FIGS. 1 and 2) may be included in the system 300 such that the patients 202 may include the patient 202a as discussed above referred to such as a first patient 202a. The patients 202 including the first patient 202a are allowed to create a marketplace for selling of the computerized records, at least in part, or for authorizing access for limited use of the computerized records, at least in part, upon being registered with the at least one computerized records data store 302 or the server 204 through the sign in scheme 210, as discussed above.

Figure 8:
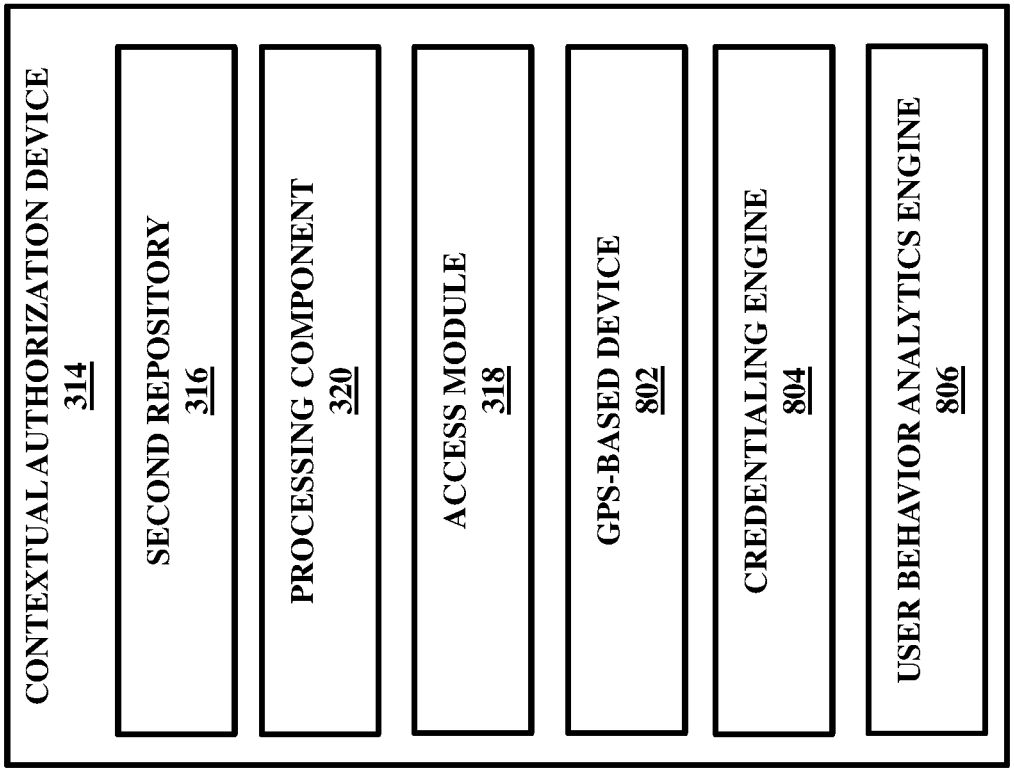
FIG. 8 illustrates a contextual authorization device, according to some embodiments herein.

FIG. 8 illustrates an example of the contextual authorization device 314 in detail, in an embodiment of the invention. The contextual authorization device 314 may be configured to authorize access to the external device 208 for the computerized records at least in part. The contextual authorization device 314 includes the database 316 storing the custom rules digitally dictating the access rights and levels for the external device 208 based on static information associated with the external device 208 and based on dynamically changing contextual information of the external device 208 and its associated entity. The database 316 has been discussed already above.

The contextual authorization device 314 further includes a Global Positioning System (GPS)-based tracking device 802 for tracking dynamically changing geo-location of the external device 208. For example, at a particular time, the external device 208 may be situated in a hospital, at other time the external device may be situated in a pharmacy or a lab or at home. When the external device 208 sends a request to access the computerized records at least in part, the GPS-based tracking device 802 may receive the geo-location of the external device 208 too along with the request. The GPS-based tracking device 802 may regularly monitor the external device 208 for its location.

The custom rules may define a set of location types and associated access levels such that a few different location types may be a hospital, a nursing center, a pharmacy, home, a lab, and the like. Each of the location types may be associated with specific levels of success and specific types of computerized records accessible from a particular type of location. For example, the hospital as a location type may be indicative of allowing a complete access to computerized records, a lab as a location type may be indicative of allowing to access digital medical records that relate to tests and diagnosis reports and doctor prescriptions, a pharmacy as a location type may be indicative of allowing to access digital medical prescriptions only. When the external device 208 is noted to be present at home, the external device 208 may be allowed to access only limited information. The various location types may be identified based on the geo-location signifying the location type and accordingly inform the access module 318 to provide authorization of the computerized records, at least in part, based on the level of access allowed in view of the location type, if the external device meets other authorization criteria. The custom rules may define different rights for different location types as identified from the geo-location of the external device 208 such that the different rights may define either one of an outright denial or approval of the access or limiting the access to one or more types of digital records based on the location types, in an embodiment. The GPS-based tracking device 802 may generate a first signal indicative of the geo-location associated with the external device 208 which may be transmitted to the access module 318 for the access module 318 to determine a location type of the external device 208, level of access allowed accordingly and nature of computerized records allowed to be accessed by the external device 208.

The contextual authorization device 314 may further include a credentialing engine 804 to determine a crowdsourced credentialing score associated with an entity associated with the external device 208. The crowdsourced credentialing score is determined based on credentialing of a digital profile of the entity by a plurality of respondents such that the crowdsourced credentialing score is indicative of trustworthiness of the external device 208. The custom rules may be defined to allow authorization of the external device 208 only when the entity associated with the external device 208 possesses at least a minimum threshold score. The credentialing engine 804 may determine the crowdsourced credentialing score associated with the entity connected with the external device 208 and generate a second signal. The second signal may be transmitted to the access module 318 for the access module 318 to compare the determined crowdsourced credentialing score with the minimum threshold score and accordingly allow or reject authorization to access the computerized records, at least in part, either entirely or only limited to particular nature of the computerized records.

Figure 9:
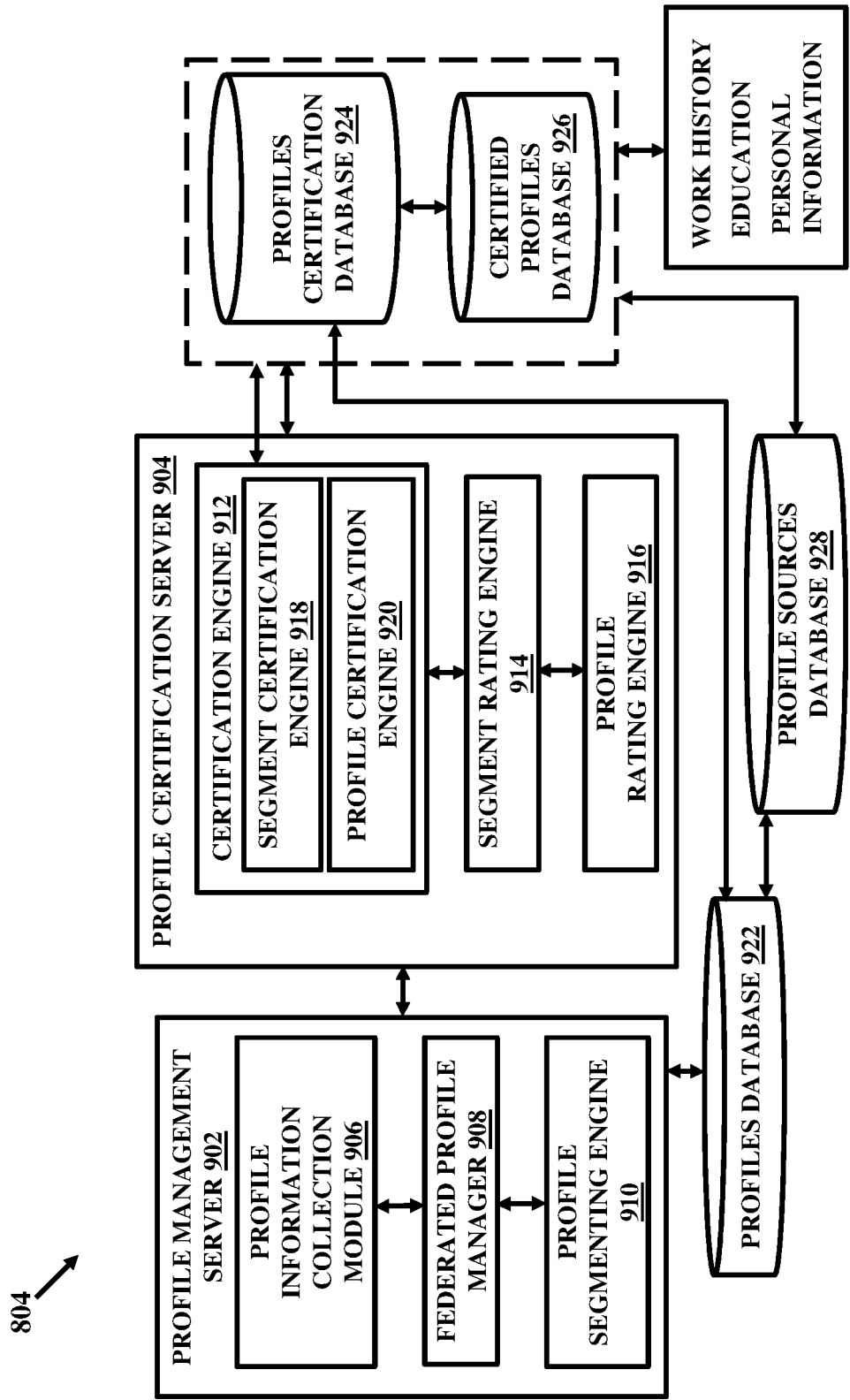
FIG. 9 illustrates an example of credentialing engine, according to the embodiments herein.

FIG. 9 illustrates an example of the credentialing engine 804 configured to generate the credentialing score, in an embodiment of the present invention.

The credentialing engine 804 may include a profile management server 902 and a profile certification server 904. The profile management server 302 includes a profile information collection module 906, a federated profile manager 908, and a profile segmenting engine 910.

The profile information collection module 906 may be configured to generate information about a plurality of entities similar to the entity associated with the external device 208. In some embodiments, the profile information collection module 906 can be disposed separately from the federated profile manager 908; while in other embodiments it can be included in or coupled to the federated profile manager 908. The profile information pertaining to profiles of the plurality of entities can be generated by distributing application forms through a graphical user interface accessible by the entities such that the entities can fill the forms and submit with the credentialing engine 804. The information can be transformed in the form of profiles by the federated profile manager 908. The segmenting engine 910 may then use the profiles information and perform the task of segmenting of the overall profiles into the federated profiles associated with each of the entities.

The profile certification server 904 may be communicatively coupled to or included in the profile management server 902. The profile certification server 904 may include a certification engine 912, a segment rating engine 914, and a profile rating engine 916. The certification engine 912 may further include a segment certification engine 918 and a profile certification engine 920.

The segment certification engine 918 may be configured to facilitate credentialing or certification of the federated profiles associated with the profiles associated with each of the entities connected to the external system 208. The segment certification engine 918 is configured to allow a plurality of crowdsourced respondents to respond to the federated profiles associated with the profiles of the entities and credential them. The credentialing of each of the federated profiles associated with the profiles of an entity contributes to credentialing of the entire profile of the entity upon collation of the credentialed federated profiles. As more and more persons or respondents from the plurality of crowdsourced respondents verify the information in the federated profiles, the trust associated with credentialing of the respective federated profiles increases. Therefore, the crowdsourcing may allow credentialing of the federated profiles to a higher degree of accuracy and reliability. Since the discrete federated profiles associated with the entity are credentialed from the plurality of crowdsourced respondents, the credentialing defines a high level of accuracy and may be considered as highly authentic and reliable and acceptable by third parties or agencies.

The segment certification engine 918 is adapted to certify the stored federated profiles relating to the entities who must have their credentials verified. According to some embodiments herein, the number of sources credentialing a particular federated profile may be associated with each of the segments to indicate a level of accuracy of the credentialing information. Also, the relevant information about credentialing such as who credentialed, when credentialed may also be associated with each credentialing of each of the federated profiles so that an authenticity may be judged by associating an overall impact of the federated profiles' credentialing, number of times credentialed, and trust factor about the source who verified and relevance about the source and time when verified. Therefore, in such embodiments, a multi-scaled and cumulative score may be determined and multi-scaled and cumulative credentialing may be done based on the multi-scaled cumulative score determined.

The information pertaining to credentialing of the individual federated profiles of a profile associated with an entity may influence an overall credentialing of the profile. For example, individual credentialing of the federated segments may contribute to the overall profile credentialing such that the credentialing of the overall profile may depend on each of the federated profiles' credentialing with a weightage attached to each credentialing of the federated profiles. The collated contribution considering weightage effect of each credentialing finally decides credentialing of the overall profile. The task of credentialing the overall profile associated with an entity may be performed by the profile certification engine 920. For example, the profile certification engine 920 may facilitate credentialing of the profile in its entirety based on the collated effect of credentialing of the federated profiles associated with the profile of the entity. The profile certification engine 920 may receive information pertinent to credentialing of each of the federated profiles associated with the overall profile and then associate the defined weightages to each of the federated profiles and perform cumulative credentialing of the overall profile. In an embodiment, the weightages may be determined based on parameters defined by a service provider who operates the credentialing engine 804. In such embodiments, the weightages may be defined based on for example past experiences or current understanding about significance of accuracy of credentialing for different segments. For example, the accuracy of credentialing may be more important for work history than information pertinent to hobbies of a professional when applying for a job. Therefore, the objective use of the credentialing information may influence determination of the weightages and hence the overall credentialing. Therefore, a score indicative of the influence of the objective may be associated for the credentialing purposes in some embodiments. In some embodiments, the weightages may be defined by an agency requiring the credentialing information. Therefore, in such cases, the profile certification engine 920 may perform credentialing of the common profile in a custom defined manner and also in association with the objective score.

The profile certification server 904 further includes the segment rating engine 914. The segment rating engine 914 is configured to associate a rating to each of the credentialed federated profiles based on credentialing from the crowdsourced plurality of respondents and depending on a level of accuracy and trust associated with the credentialing of the federated profiles. The rating may depend on who credentialed a federated profile, when was a profile credentialed, how many times a profile was credentialed, how many unique credentials are done, relevance of respondents credentialing the federated profile, relationship of the respondents with the entity such as of the credentialed federated profile, and the like.

The profile certification server 904 may further include the profile rating engine 916. The profile rating engine 916 is configured to associate a rating to an entire profile based on credentialing of each of the federated profiles and ratings associated with each of the federated profiles as determined by the segment rating engine 914 cumulatively.

The profile management server 902 is coupled to a profiles database 922 to store information pertinent to the profiles of the plurality of entities. The profiles database 922 may be coupled to the federated profile manager 908 such that the federated profile manager 908 maintains the information stored in the profiles database 922.

The profile certification server 904 may be coupled to a profiles certification database 924. The profiles certification database 924 is configured to store information pertinent to credentialing such as certification status of the federated or overall profiles associated with the plurality of entities. For example, the certification status may include one or more of verified segment, verified profile, pending verification, verification in progress, segment rejected as incorrect, profile rejected as incorrect and the like. The profiles certification database 924 may be coupled to the profiles database 922 and the certification engine 912.

The profile certification server 904 may be coupled to a certified profiles database 926. The certified profiles database 926 may further be coupled to the profiles certification database 924. The certified profiles database 926 may be configured to store profiles that have been verified by the certification engine 912. An entity or agency may be allowed a direct access to the certified profiles database 926 based on preferences and rules defined for the entity or the agency. The entity may be one of a medical entity such as a hospital, nursing center, doctor, physician, healthcare unit, and government healthcare department, or an entity belonging to other industry such as financial sector, energy, transportation and the like or any other third-party or agency and associated with the external device 208. The certified profile or credential database 926 may further store information pertinent to one or more of work history, education, and personal demographics, affiliations to hospitals or other institutes etc. of one or more entities corresponding to one or more of verified profiles.

The profiles database 922, profiles certification database 924, and the certified profiles database 926 may be coupled to a profiles sources database 928. The profile sources database 928 may include information about a plurality of sources in the network 106 that are linked to the federated profiles associated with the plurality of the entities, and information about a plurality of sources who responds to the federated profiles for credentialing. For example, in the network 106, the plurality of respondents may credential the federated profiles and thus the profiles sources database 928 may store their details, their names, other information, their relevance and relationship with the entities associated with the federated profiles they credential and time of credentialing, and location of original credentialing or any other such information pertinent to the credentialing sources etc.

In an example, the profiles database 922, profiles certification database 924, and the certified profiles database 926 may be blockchain configured so as to allow access by the entities (and respondents) or any other agency and associated computing systems similar to the external device 208 through the distributed plurality of access points simultaneously and reflect or view reviews or any changes during review process in near real-time.

In an embodiment, the credentialing by the respondents is used to associate a rating and define a level of trust for the federated profiles and the overall profiles.

In an embodiment, the credentialing engine 804 may be contained within or coupled to the server 204 or the contextual authorization device 314. In an embodiment, an external service provider may deploy the credentialing engine 804 and provide credentialing scores to the server 204 or the contextual authorization device 314 as and when requested by the server 204 or the contextual authorization device 314 upon a request of access of the computerized records being submitted by the external system 208 or associated entity to the server 204. The credentialing engine 804 may generate the second signal indicative of the credentialing score and the trustworthiness of the external device 208 and its associated entity. The second signal may be processed by the access module 318.

Referring back to FIG. 8, the contextual authorization device 314 may include a user behavior analytics engine 806 to compare dynamically changing contextual details associated with the entity with a set of past requests indicative of historical behavior of the entity. Based on comparison of the contextual details of the entity and the associated external device 208 with their historical behavior, the user behavior analytics engine 806 may determine commonalities and mismatches in the behavior and accordingly determine an index of normality which is indicative of an extent of similarity in the contextual behavior and the historical behavior. The custom rules may be defined to allow the access only when a minimum predefined threshold of normality is noted about the external device 208 and the associated entity. The user behavior analytics engine 806 may be configured to generate a third signal indicative of the index of normality and transmit it to the access module 318 so that the access module 318 can allow authorization of the access to the external device 208 based on the index of normality alone or along with one or more other parameters as identified by the credentialing engine 804 and the GPS-based device 802.

In accordance with various embodiments, the access module 318 may allow access to the computerized records at least in part based on information contained in one or more of the first signal, second signal, and the third signal. The access module 318 may process authorization of the external device 208 for access of the computerized records, at least in part based on an input received from one or more of the GPS-based tracking device 802, credentialing engine 804, and the user behavior analytics engine 806.

The processing component 320 may create the computerized records, at least in part, based on the authorization by the access module. The processing component 320 may transform the authorized computerized records into a digital data structure readable by a scanner. The digital data structure may be a quick response (QR) code.

In an embodiment, the monetization engine 322 may include or be coupled to a document usage system 330 which includes one or more document computer systems in communication with a network of devices including the external device 208 and having a machine-accessible medium storing a plurality of program modules configured to determine document utilization information providing an indication of usage of computerized records at least in part as authorized to be accessed by the external device 208 associated with the entity. The usage may include an amount of time that the associated entity or the external device 208 has accessed particular sections of the authorized computerized records. The monetization engine 322 may calculate price value for billing to the external system based on the usage of the computerized records, at least in part. In an embodiment, the computerized records may be classified into discrete types and the monetization engine 322 may be configured to associate a price value with the authorized computerized records based on the usage by the external device 208 based on the type the authorized computerized records as accessed by the external device 208 are classified into.

Figure 10:
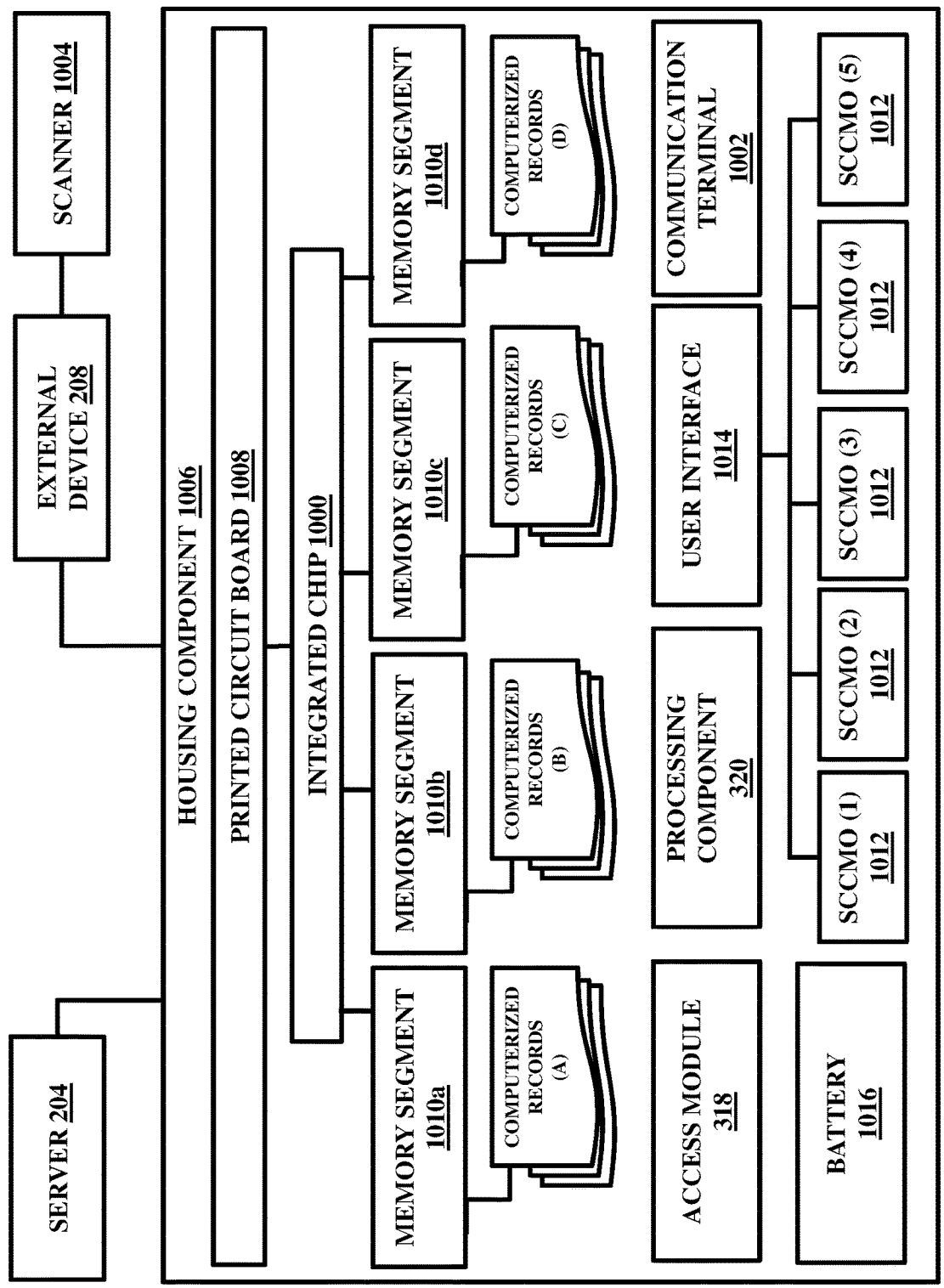
FIG. 10 illustrates an integrated chip, according to some embodiments herein.
Figure 11:
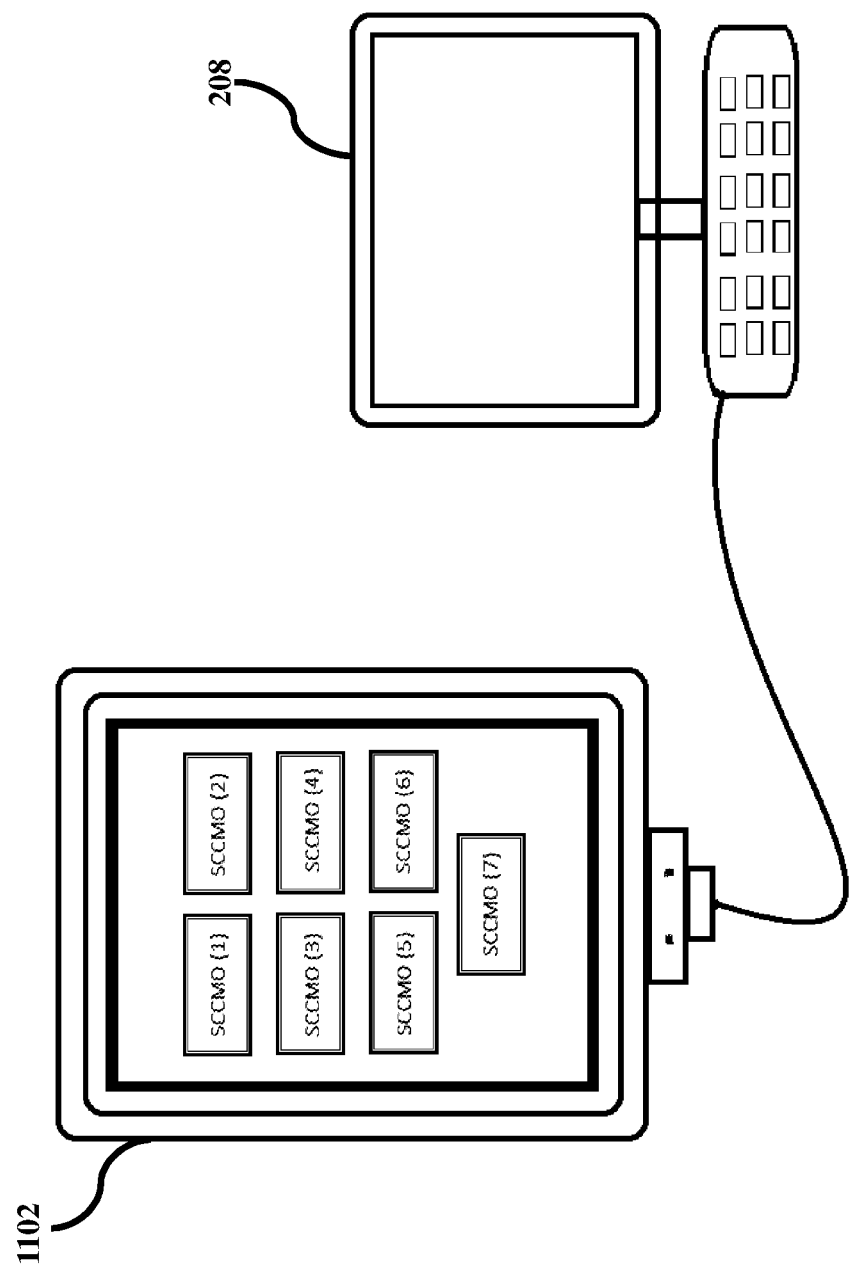
FIG. 11 illustrates an exemplary portable device encapsulating the integrated chip connected with the external device, according to some embodiments herein.

FIG. 10 illustrates an exemplary integrated chip 1000 configured as a portable device 1102 (labeled and shown in FIG. 11) capable of communicating with the external system 208 through a communication link made between a communication terminal 1002 of the integrated chip (or the portable device) 1000 and the external system 208 or an associated reader connected with the external system such as a scanner 1004. FIG. 11 illustrates another view of the portable device 1102 connected with the external device 208, in an embodiment.

The integrated chip 1000 may be contained within a portable device housing component 1006. The integrated chip 1000 may be mounted on a printed circuit board 1008 within the portable device housing component 1006.

The integrated chip 1000 may contain a plurality of memory segments 1010a, 1010b, 1010c, and 1010d located on the printed circuit board 1008 as discrete but connected components of the integrated chip 1000. The memory segments 1010a-d may each encapsulate computerized records of a particular type requiring a particular level of access authorization by the access module 318. For example, the memory segment 1010a may contain digital prescription records, the memory segment 1010b may contain digital lab records, the memory segment 1010c may contain digital demographic records, the memory segment 1010d may contain digital medical historical records, and the like. Each of the type of records may be defined as belonging to a particular category of computerized records by associating an identifier such that each of the type of records may be associated with a particular level of authorization requiring a particular level of trustworthiness and/or authorization as identified by one or more of the GPS-based device 802, credentialing engine 804, and the user behavior analytics engine 806. As shown, the GPS-based device 802, credentialing engine 804, and the user behavior analytics engine 806 are contained within a remote server located away from the integrated chip 1000. In an embodiment, however, the GPS-based device 802, credentialing engine 804, and the user behavior analytics engine 806 are contained within the integrated chip 1000 without limitations so that the integrated chip 1000 does not need to process authorization based on external inputs obtained from the server 204 located at a different location, instead, the integrated chip 1000 may process authorization entirely based on inputs generated by devices contained within the integrated chip 1000 and without waiting for any external communication link. As shown, the integrated chip 1000 may contain the access module 318 and the processing circuit 320. The access module 318 and the processing circuit 320 have already been discussed in conjunction with FIG. 3 above.

In an embodiment, the integrated chip 1000 is communicatively connected with the remote server 204 such that the remote server 204 may generate certain inputs for use by the access module 318 in authorizing access to the external device 208 for the computerized records at least in part. The server 204 may also contain the database 316 storing the set of custom rules digitally dictating access rights and levels for the external device 208 based on the static information associated with the external device 208 and based on the dynamically changing contextual information. In an embodiment, the access module 318 is allowed to authorize the access of the computerized records, at least in part, based on the certain inputs either received from the remote server 204 or generated within such as from the GPS-based device 802, credentialing engine 804, and the user behavior analytics engine 806, without any manual intervention. In an embodiment, alternatively, the access module 318 is allowed to authorize the access of the computerized records, at least in part, based on single click manual authorization using one of a plurality of single-click configurable menu options (SCCMO) 1012 (1-4) provided on a user interface 1014 to allow access of the computerized records of a particular type defined for a particular context. The SCCMO 1012 are discussed hereafter.

The SCCMO 1012 may be provided on the user interface 1014 and may be predefined. In an embodiment, however, a user may configure the SCCMO 1012 based on his/her requirements. The SCCMO 1012 may for example include menu options including such as for hospital, pharmacy, lab, home, and the like so that each of these The SCCMO 1012 may be associated with respective access levels defined for location at the hospital, pharmacy, lab, and the home. The user can anytime delete any of the SCCMO 1012 if it is not needed at all. The user may also edit any of the SCCMO 1012. The user may also add any new SCCMO 1012. For example, the user can add a new SCCMO 1012 for a new location 'work space'. The server 204 may store pre-defined access rights policies for specific location types and as soon as the user configures any of the SCCMO 1012 for a particular location type, the nature of computerized records along with the location type may associate specific access levels of authorization of the computerized records in such a way that only authorized computerized records, at least in part, are allowed to be accessed by the external device 208 from a particular location type for accessing particular types of records. The SCCMO 1012 may provide an easy to navigate and easy to operate user interface so that the user can perform authorizations or initiates request of authorization merely by a single click on the SCCMO 1012. For example, when the use visits a hospital, he may simply press the SCCMO 1012 defined for the hospital so that all medical records stored digitally may be authorized to be accessed by the external device 208 knowing that the hospital should have access to all forms of medical records. In a different case, however, when the user is located at a pharmacy for medicine purchases, he may press the SCCMO 1012 defined for pharmacy so that only recent and historical medical prescriptions may be allowed to be accessed by the external device 208 associated with the pharmacy. The server 204 may make determinations about what types of records need to be allowed for the access based on the SCCMO 1012 pressed by the user. In accordance with the illustrated embodiment. Only four menu options are illustrated as part of the SCCMO 1012, however, the user can add more menu options or delete any of the existing menu options.

The SCCMO 1012 may be defined to provide authorization request in a single click such that a single-click configurable menu option of the plurality of SCCMO 1012 is defined to authenticate only a particular type of computerized record with a particular level of access. The level of access may include such as one of a full access, limited access, and no access such that the level of access is defined based on one or more of geo-location, credentialed score, and user behavior analytics of the external device 208 and the integrated chip 1000. The access module 318 is allowed to authorize the access of the computerized records, at least in part, either based on the inputs received from the remote server 302 without any manual intervention or alternatively based on single click manual authorization using one of the plurality of single-click configurable menu options 1012 to allow access of the computerized records of a particular type defined for a particular context.

In an embodiment, the computerized records data store 302 storing the computerized records may be contained within the server 204 so that upon authorization processing by the access module 318, the processing component 320 may extract the computerized records, at least in part from the server 204. In an embodiment, however, the computerized records data store 302 may be contained within the integrated chip 1000.

The integrated chip 1000 may be connected with a battery 1016 for providing power source for functioning of the portable device 1102.

The communication terminal 1002 may be configured to establish a communication link between the integrated chip 1000 and the external device 208 as soon as any of the plurality of single-click configurable menu options 1012 is pressed by the user. In an embodiment, the communication terminal 1002 is a near-field communication (NFC) terminal or channel with one or more NFC points or taps or interaction points configured to establish a communication link between the integrated chip 1000 and the external device 208 as soon as any of the plurality of single-click configurable menu options 1012 is pressed by the user and the one or more NFC taps is activated.

In an example, the integrated chip 1000 communicates with the external device through the NFC channel wherein the NFC channel may include the one or more NFC points to connect with the external device 208. The integrated chip 1000 interacts with the NFC point of the NFC channel to share authorization request and/or the computerized records, at least in part and initiate a digital information exchange activity. In an embodiment, the NFC channel is a short-range communication network, wherein range of the NFC channel is 100 meters so that the external device 208 is located within proximity of 100 meters from the integrated chip 1000. In an embodiment, the NFC network channel is a Bluetooth™ network.

In an embodiment, the NFC channel is a short-range communication network, wherein range of the NFC network is approximately thirty feet so that the external device 208 is located within an approximate proximity of thirty feet from the integrated chip 1000 for communication to happen. In an embodiment, the NFC network is based on a Radio Frequency Identification (RFID) system such that the external device 208 includes an RFID tag capable of being read by a reader communicatively coupled to or included within the integrated chip 1000 or the external device 208 includes an RFID reader configured to read RFID tags associated with the integrated chip 1000.

In an embodiment, the NFC network channel is a Body Area Network (BAN) or a wireless sensor network associated with the external device 208 that is wearable by a human in some embodiments. The BAN includes a gateway to reach the communication terminal 1002 through the external device 208. The BAN may include such as monitoring sensors, motion detectors, and other sensing circuits associated with a subject. The BAN is further linked communicatively to a processing circuit and includes a power source and a transceiver (not shown) for communicating with the integrated chip 1000 through the gateway. The external device 208 includes the NFC taps and links which may be programmable by NFC applications.

In an embodiment, the communication terminal 1002 may connect with the external device 208 through a wide network such as a WiFi or internet such that the network allows interconnection and automation among the integrated chip 1000 and the external device 208. In an embodiment, the communication terminal 1002 may be a WiFi hotspot with one or more WiFi taps configured to establish a communication link between the integrated chip 1000 and the external device 208 as soon as any of the plurality of single-click configurable menu options 1012 is pressed by the user and the one or more WiFi taps is activated.

In an embodiment, the communication terminal 1002 may be configured to connect with the external device 208 by establishing the communication link with the external device 208 or any other communication terminal integrated within or connected with the external device 208. In an example, the external device 208 may be a computing device associated with the entity and configured to initiate a request to access the computerized records, at least in part and also establish the communication link with the communication terminal 1002.

In an example, the external device 208 may be a swipe machine configured to receive a portion of the integrated chip 1000 and read digital information such that the swipe machine may establish the communication link with the communication terminal 1002. In an example, the external device 208 may be a scanner such as the scanner 1004 which may include the swipe machine or any other digital information reader such as radio frequency identification device (RFID) reader configured to read the integrated chip 1000 for extracting the computerized records, at least in part, according to authorization by the authorization module. The scanner may be configured to initiate a request to access the computerized records, at least in part and also establish the communication link with the communication terminal 1002. The scanner 1004 may include an NFC terminal, in an embodiment, to establish the NFC link between the scanner 1004 and the communication terminal 1002 of the integrated chip 1000.

In various examples, the communication terminal 1002 may establish communication with the external device 208 through various other channels or standards such as but not limited to satellite navigation, GPS signals, Geofencing, ZigBee networking, and the like.

In an example, the scanner 1004 may be configured to read the digital data structure which may be in the form of a QR (quick response) code readable by the scanner 1004 without limitations.

In an example, the embodiments herein can provide a computer program product configured to include a pre-configured set of instructions, which when performed, can result in actions as stated in conjunction with the method(s) described above. In an example, the pre-configured set of instructions can be stored on a tangible non-transitory computer readable medium. In an example, the tangible non-transitory computer readable medium can be configured to include the set of instructions, which when performed by a device, can cause the device to perform acts similar to the ones described here.

The embodiments herein may comprise a computer program product configured to include a pre-configured set of instructions, which when performed, can result in actions as stated in conjunction with the methods described above. In an example, the pre-configured set of instructions can be stored on a tangible non-transitory computer readable medium or a program storage device. In an example, the tangible non-transitory computer readable medium can be configured to include the set of instructions, which when performed by a device, can cause the device to perform acts similar to the ones described here. Embodiments herein may also include tangible and/or non-transitory computer-readable storage media for carrying or having computer executable instructions or data structures stored thereon.

Generally, program modules include routines, programs, components, data structures, objects, and the functions inherent in the design of special-purpose processors, etc. that perform particular tasks or implement particular abstract data types. Computer executable instructions, associated data structures, and program modules represent examples of the program code means for executing steps of the methods disclosed herein. The particular sequence of such executable instructions or associated data structures represents examples of corresponding acts for implementing the functions described in such steps.

The techniques provided by the embodiments herein may be implemented on an integrated circuit chip 1000. The chip design is created in a graphical computer programming language, and stored in a computer storage medium (such as a disk, tape, physical hard drive, or virtual hard drive such as in a storage access network). If the designer does not fabricate chips or the photolithographic masks used to fabricate chips, the designer transmits the resulting design by physical means (e.g., by providing a copy of the storage medium storing the design) or electronically (e.g., through the Internet) to such entities, directly or indirectly. The stored design is then converted into the appropriate format (e.g., GDSII) for the fabrication of photolithographic masks, which typically include multiple copies of the chip design in question that are to be formed on a wafer. The photolithographic masks are utilized to define areas of the wafer (and/or the layers thereon) to be etched or otherwise processed.

The resulting integrated circuit chip 1000 can be distributed by the fabricator in raw wafer form (that is, as a single wafer that has multiple unpackaged chips), as a bare die, or in a packaged form. In the latter case the chip is mounted in a single chip package (such as a plastic carrier, with leads that are affixed to a motherboard or other higher level carrier) or in a multichip package (such as a ceramic carrier that has either or both surface interconnections or buried interconnections). In any case the chip is then integrated with other chips, discrete circuit elements, and/or other signal processing devices as part of either (a) an intermediate product, such as a motherboard, or (b) an end product. The end product can be any product that includes integrated circuit chips, ranging from toys and other low-end applications to advanced computer products having a display, a keyboard or other input device, and a central processor.

The embodiments herein can include both hardware and software elements. The embodiments that are implemented in software include but are not limited to, firmware, resident software, microcode, etc.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

Figure 12:
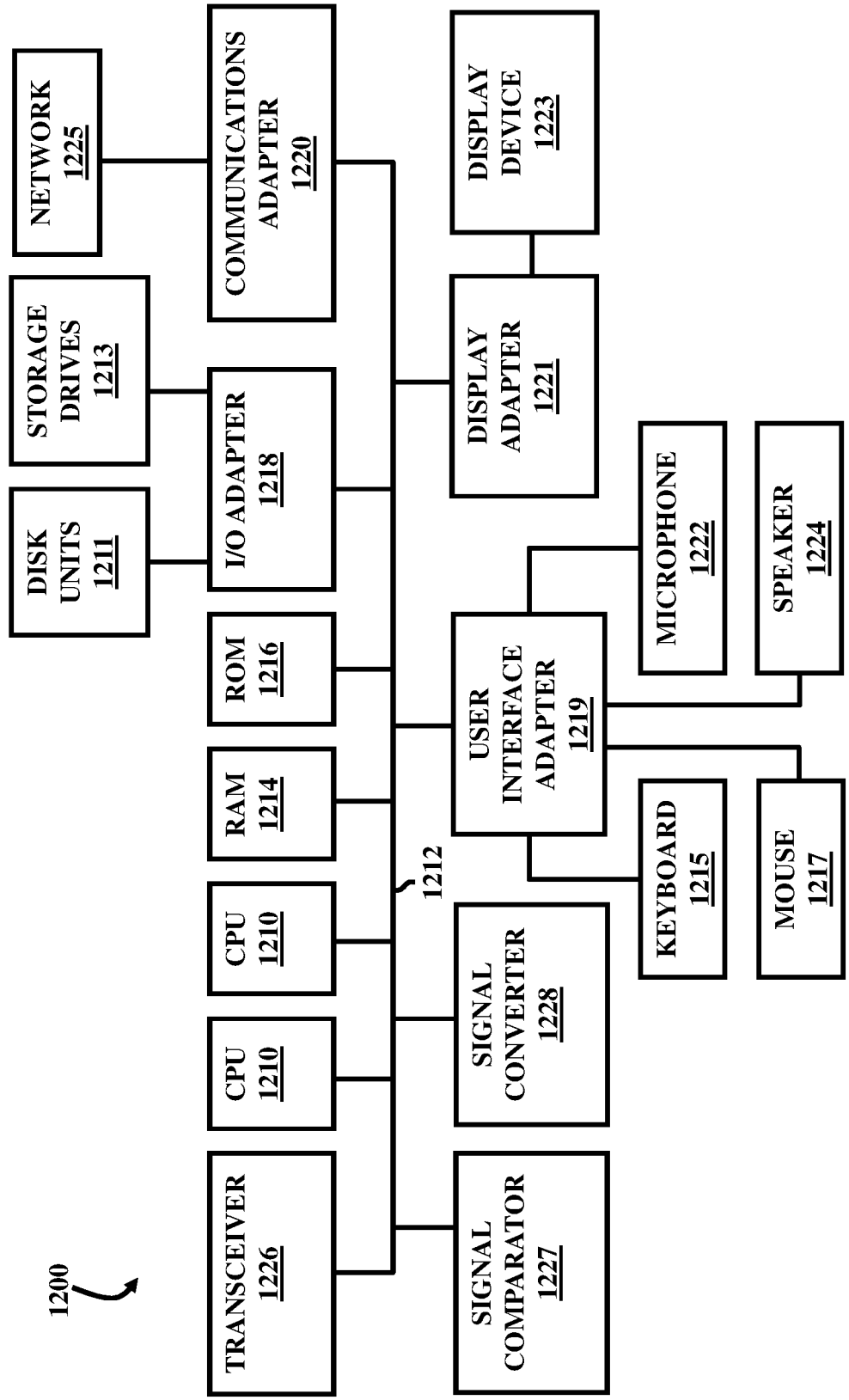
FIG. 12 illustrates a representative hardware environment for practicing various embodiments herein.

A representative hardware environment for practicing the embodiments herein is depicted in FIG. 12, with reference to FIGS. 1 through 11. This schematic drawing illustrates a hardware configuration of an information handling/computer system 1200 in accordance with an exemplary embodiment herein. The system 1200 comprises at least one processor or central controller (CPU) 1210. The CPUs 1210 are interconnected via system bus 1212 to various devices such as a random access memory (RAM) 1214, read-only memory (ROM) 1216, and an input/output (I/O) adapter 1218. The I/O adapter 1218 can connect to peripheral devices, such as disk units 1211 and storage drives 1213, or other program storage devices that are readable by the system. The system 1200 can read the inventive instructions on the program storage devices and follow these instructions to execute the methodology of the embodiments herein. The system 1200 further includes a user interface adapter 1219 that connects a keyboard 1215, mouse 1217, speaker 1224, microphone 1222, and/or other user interface devices such as a touch screen device (not shown) to the bus 1212 to gather user input. Additionally, a communication adapter 1220 connects the bus 1212 to a data processing network 1225, and a display adapter 1221 connects the bus 1212 to a display device 1223, which provides a GUI (e.g., a gadget) in accordance with the embodiments herein, or which may be embodied as an output device such as a monitor, printer, or transmitter, for example. Further, a transceiver 1226, a signal comparator 1227, and a signal converter 1228 may be connected with the bus 1212 for processing, transmission, receipt, comparison, and conversion of electric or electronic signals.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. A system for providing access authorization to an external device for access to computerized records of multiple types in a computerized records data store, the system comprising:
    a portable device;
    a communication terminal communicatively linking the portable device to the external device;
    a plurality of memory segments in the portable device and comprising a specified type of computerized records that have been authorized for access by the external device;
    a user interface on the portable device and comprising a plurality of single-click computer-executable menu options defined by a location type comprising particular levels of access to particular types of computerized records that allow authorizing access to the external device by selecting the location type for the external device;
    an access module in the portable device and comprising electronic circuits that execute computer logic instructions that authorizes that access to computerized records by the external device, wherein the electronic circuits of the access module receive a first signal comprising a geo-location associated with the external device, wherein the electronic circuits of the access module determine levels of access and types of computerized records in the computerized records data store that are allowed to be accessed by the external device, wherein the electronic circuits of the access module extract and place data structures comprising the computerized records that are allowed to be accessed by the external device in one or more of the plurality of memory segments for access by the external device, and wherein the electronic circuits of the access module execute computer logic instructions that authorize the external device to access the computerized records based on the geo-location associated with the external device; and
    an integrated circuit chip in the portable device and containing a processing component that executes computer logic instructions that create the computerized records in the plurality of memory segments,
    wherein the electronic circuits of the access module execute computer logic instructions that specifies the level of access and type of computerized records in the computerized records data store that are to be extracted and placed in the plurality of memory segments for access by the external device,
    wherein the processing component executes computer logic instructions that (i) extract the computerized records from the computerized records data store based upon authorization instructions from the electronic circuits of the access module, and (ii) store extracted computerized records in the plurality of memory segments,
    wherein the electronic circuits of the access module execute computer logic instructions that process the authorization using the geo-location of the external device in conjunction with custom computer-executable rules digitally dictating access rights and levels for the external device based on static information associated with the external device and based on dynamically changing contextual information stored in a database storing the custom computer-executable rules, wherein the electronic circuits of the access module execute computer logic instructions that process the authorization using the location type of the external device in conjunction with the custom computer-executable rules when the location type of the external device is selected by pressing at least one of the plurality of single-click computer-executable menu options, wherein the custom computer-executable rules define different rights for different location types based on the geo-location of the external device or as identified by selecting at least one of the plurality of single-click computer-executable menu options, wherein the different rights define either one of an outright denial or approval of access or limiting the access to the computerized records based on the location types, wherein the communication terminal provides a communication link through a near-field communication (NFC) or a WiFi communication protocol between the portable device and the external device when at least one of the plurality of single-click computer-executable menu options is selected, and wherein the electronic circuits of the access module execute computer logic instructions that authorize access of the computerized records based on the geo-location of the external device or based on the location type for the external device identified by selecting at least one of the plurality of single-click computer-executable menu options that grants access to authorized types of the computerized records.

2. The system of claim 1, wherein the plurality of single-click computer-executable menu options comprise a single-click computer-executable menu option for a hospital terminal computer, a single-click computer-executable menu option for a pharmacy terminal computer, a single-click computer-executable menu option for a lab terminal computer such that each of the plurality of single-click computer-executable options are defined by respective location types associated with particular levels of access to particular types of computerized records as defined through associated geo-locations.

3. The system of claim 1, comprising a Global Positioning System (GPS)-based tracking device operatively connected to the portable device, wherein the GPS-based tracking device tracks the geo-location of the external device.

4. The system of claim 1, wherein the processing component executes computer logic instructions that transform the authorized computerized records into a digital data structure readable by a scanner communicatively connected with the external device.

5. The system of claim 4, wherein the digital data structure comprises a QR (quick response) code readable by the scanner.

6. The system of claim 1, wherein the integrated circuit chip comprises the plurality of memory segments, wherein the external device comprises a scanner, and wherein the scanner comprises a swipe machine reader that electronically reads the integrated circuit chip and executes computer-executable instructions that extract computerized records according to authorization by the access module.

\* \* \* \* \*